United States Patent [19]
Fenn et al.

[11] Patent Number: 5,686,726
[45] Date of Patent: Nov. 11, 1997

[54] COMPOSITION OF MATTER OF A POPULATION OF MULTIPLY CHARGED IONS DERIVED FROM POLYATOMIC PARENT MOLECULAR SPECIES

[75] Inventors: John Bennett Fenn, Branford, Conn.; Chin-Kai Meng, Hockessin, Del.; Matthias Mann, Odense, Denmark

[73] Assignee: John B. Fenn, Richmond, Va.

[21] Appl. No.: 911,405

[22] Filed: Jul. 10, 1992

Related U.S. Application Data

[62] Division of Ser. No. 773,776, Oct. 10, 1991, Pat. No. 5,130,538, which is a continuation of Ser. No. 683,105, Apr. 10, 1991, abandoned, which is a continuation of Ser. No. 354,393, May 19, 1989, abandoned.

[51] Int. Cl.$^6$ .................................................. H01J 49/00
[52] U.S. Cl. ................................................ 250/282; 250/281
[58] Field of Search ................................ 250/282, 281, 250/288, 288 A, 423 R

[56] References Cited

U.S. PATENT DOCUMENTS

| | | | |
|---|---|---|---|
| 3,639,757 | 2/1972 | Caroll et al. | 250/282 |
| 4,542,293 | 9/1985 | Fenn et al. | 250/288 |
| 4,701,419 | 10/1987 | Morris | 250/282 |
| 5,072,115 | 12/1991 | Zhou | 250/281 |

*Primary Examiner*—Jack I. Berman
*Assistant Examiner*—Kiet T. Nguyen

[57] ABSTRACT

This invention describes the production of mass spectra which contain a multiplicity of peaks. The component ions of these peaks, which are multiply charged, are formed by dispersing a solution containing an analyte into a bath gas as highly charged droplets. The analyte is generally a compound of high molecular weight and is of biochemical interest. The invention also describes methods for calculating the molecular weight of the analyte from the measured mass values of the highly charged ions.

112 Claims, 10 Drawing Sheets

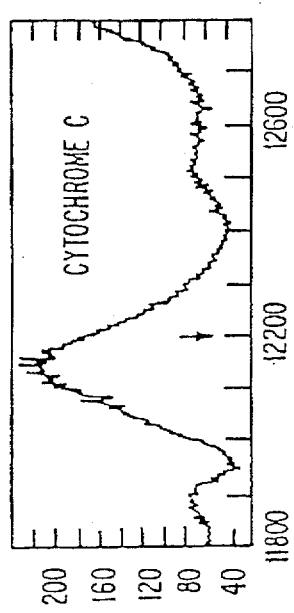
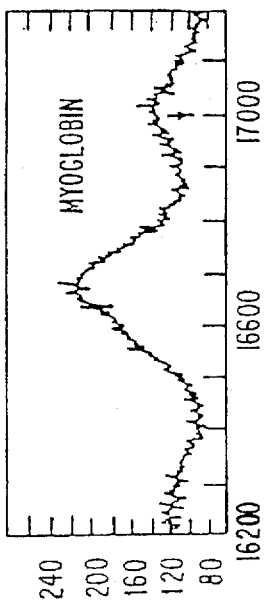
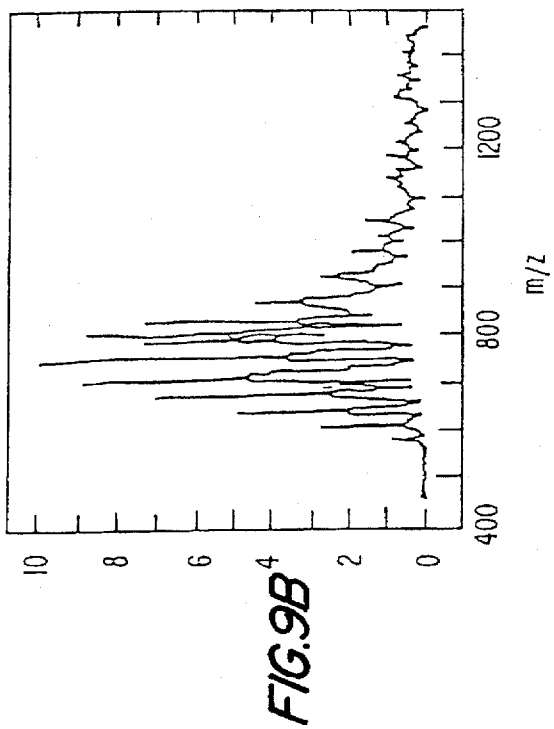
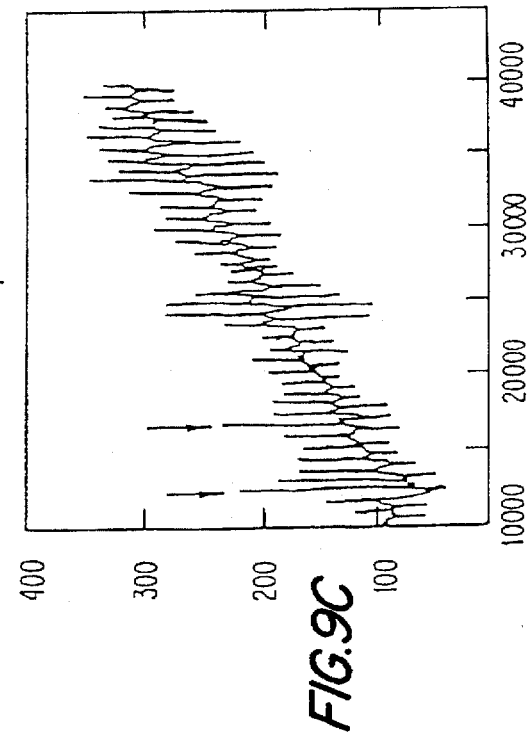
FIG.9A CYTOCHROME C + MYOGLOBIN
0.5 mg/ml each
In 1:1 MeOH-ACN, H2O 100 ppm TFA
8 μl/min 30 sec single scan

COMPOSITION OF MATTER OF A POPULATION OF MULTIPLY CHARGED IONS DERIVED FROM POLYATOMIC PARENT MOLECULAR SPECIES

This is a divisional of application Ser. No. 07/773,776, filed Oct. 10, 1991, now U.S. Pat. No. 5,130,538 issuing Jul. 14, 1992 which is a file wrapper continuation of U.S. Ser. No. 07/683,105 filed Apr. 10, 1991, which is a file wrapper continuation application of Ser. No. 07/354,393 filed May 19, 1989, both now abandoned.

RIGHTS STATEMENT

The U.S. Government has a paid-up license to this invention and the fight in limited circumstances to require the patent owner to license others on reasonable terms as provided for by the terms of Grant No. 2RO1 GM31660-04A1 awarded by the National Institutes of Health.

TECHNICAL FIELD

This invention relates to improvements in a method for mass spectrometric analysis of chemical compounds in solution. In particular it is concerned with determining the mass or molecular weight of large fragile solute species with greater speed, convenience and accuracy than has been possible by previous methods. The invention also relates to new compositions of matter comprising populations of ions having a multiplicity of charges.

BACKGROUND ART

Mass spectrometry consists in "weighing" individual molecules by transforming them intact into ions in vacuo and then measuring the response of their trajectories to various combinations of electric and/or magnetic fields. Attempts to extend the application of mass spectrometric methods to the analysis of very large polar organic and bio-organic molecules have long been frustrated by the difficulties of transforming such molecules into ions. The analytical advantages of mass spectrometry for such parameters as detection sensitivity, accuracy of mass measurement and abundance determinations cannot be realized if the prerequisite ions cannot be formed. Large polar molecules generally cannot be vaporized, even in vacuo, without extensive, even catastrophic, decomposition. Consequently, one cannot apply the classical methods of ionization based on gas phase encounters of the molecule to be ionized with electrons as in Electron Ionization (EI), photons as in Photo Ionization (PI), other ions as in Chemical Ionization (CI), or excited atoms or molecules as in Auger Ionization (AI). Such encounters can form ions from a neutral molecule by a variety of mechanisms including removal or attachment of an electron and removal or attachment of a positively charged entity, typically a proton.

In recent years a number of so-called "soft" ionization methods have been developed which with varying degrees of success have been able to produce intact ions from molecular species of ever increasing size. One class of such methods is based on very rapid deposition of energy on a surface over which the species to be analyzed (analyte) has been dispersed. The idea is, as first suggested by Beuhler et al, Journal of American Chemical Society, 96, 3990 (1974), that if the heat required is applied rapidly enough, vaporization may occur before decomposition has a chance to take place. The rapid heating methods now in use include Plasma Desorption (PD), in which disintegration of a radioactive isotope, usually Californium-252, produces a small blob of plasma on the surface from which a few intact ions of analyte emerge; Secondary Ionization Mass Spectrometry (SIMS), hereafter referred to as Fast Ion Bombardment (FIB), in which the analyte-containing surface is bombarded by ions, e.g. Cs+, accelerated to energies in the tens of kilovolts; Fast Atom Bombardment (FAB) in which the accelerated ions are neutralized by charge exchange before they strike the surface; Laser Desorption (LD) in which photons comprise the vehicle for depositing energy on the surface. These methods have been able to produce intact ions from remarkably large analyte species even though, except for LD, they are highly irreversible and characterized by brute force. To date, intact ions have been produced from bio-organic compounds with molecular weights on the order of 210,000 with LD (M. Kurds and F. Hillenkamp, paper presented at 11th *International Mass Spectrometry Conference*, Bordeaux, France 1988; cf. Analytical Chemistry (1988) 60, 2299), 24,000 with FAB (or FIB) (M. Barber and B. N. Green, Rapid Communications in. Mass Spectrometry. (1987) 1, 80) and 45,000 with PD (G. Jonsson, P. Hakansson, A. Hedin, D. Fenyo, B. Sundqvist, H. Bennich and P. Roepstorff, Rapid Commun. Mass Spectrom. in press). The ion currents in these methods have been very small and except for LD decrease rapidly with increasing molecular weight. When the ions get very large their detection with multipliers requires post-acceleration voltages that are often awkwardly high. Except possibly with LD, the ions produced often have high levels of internal excitation which can result in substantial peak broadening due to predissociation.

Quite different in practice and principle from these "violent" ionization methods are techniques that use very strong electrostatic fields to extract ions from a substrate. In so called Field Desorption (FD) ionization the analyte molecules are applied to a fine wire on whose surface is disposed an array of sharp pointed needles or "whiskers." When the wire is placed in a vacuum system and a high voltage is applied while it is carefully heated, the analyte molecules will desorb as ions from the tips of the needles where the effective field strength is very high. Even though it can transform very involatile analytes into ions in vacuo FD has not become widely used, in part because sample preparation is tedious, in part because of difficulties in adjusting the wire to just the fight temperature and voltage, and in part because the desorbed ions have such high energies that relatively expensive magnetic sector analyzers must be used for mass determination. In so-called Electrohydrodynamic Ionization (EH) analyte is dissolved in a non-volatile liquid (e.g. glycerol) and injected into an evacuated chamber through a small capillary tube maintained at high voltage. The solvent liquid must have a low vapor pressure so that it won't "freeze-dry" from rapid evaporation into vacuum. Solute ions, along with molecules and clusters of solvent, are desorbed from the emerging liquid by the high field at its surface and can be mass analyzed. EH has not been widely practiced, in part because few liquids that have low vapor pressure are good solvents for large polar bio-organic compounds, in pan because the desorbed ions are usually solvated with one or more molecules of the solvent, and in pan because they often have a wide distribution of energies. Moreover, as in the case of FD, the product ions have high energies and require magnetic sector analyzers.

In the past few years there has emerged a new family of ionization techniques that also make use of high electric fields to desorb ions. These techniques differ from FD and EH in that desorption is from small charged droplets of solution into an ambient bath gas instead of into vacuum.

The required high fields at the droplet surface result from the increasing charge density and decreasing radius of curvature of the droplet surface as the solvent evaporates. A portion of the bath gas containing the desorbed ions is then admitted through a small orifice into a vacuum system containing an appropriate mass analyzer. The bath gas acts as a very effective moderator, i.e. it maintains both internal and translational energies of the ions at levels corresponding to the bath gas temperature which is rarely high enough to cause thermal decomposition of even labile bio-organic compounds. In Thermospray (TS) ionization which was developed by Vestal and his colleagues the sample solution is passed through a heated tube whose walls are hot enough to vaporize most of the solvent. (J. Amer. Chem. Soc. (1980) 102, 5931). The consequent rapid expansion of solvent vapor produces acceleration and shear forces that atomize the remaining liquid. Thus there emerges from the end of the tube a supersonic jet of superheated solvent vapor in which the remaining sample solution that was atomized is dispersed as small droplets, equal numbers of which are positively and negatively charged. The charging is a result of statistical fluctuations in the distribution of cations and anions as the liquid is nebulized. In a somewhat equivalent technique, called Atmospheric Pressure Ion Evaporation (APIE) by its originators, J. V. Iribarne and B. A. Thomson, droplets are produced by intersecting a flow of sample solution with a high speed jet of air. (J. Chem. Phys. (1976) 64, 2287 and ibid. (1979) 71, 4451). In this discussion APIE will be referred to by the more convenient term Aerospray (AS) to indicate that it is based on pneumatic nebulization of the sample liquid. As in TS the charging is due to statistical fluctuations in the distribution of cations and anions among the droplets during atomization of the liquid. It was found that an induction electrode, at a potential of 3 kilovolts and placed near the atomization region, greatly increased the total ion current. Moreover, all the resulting droplets and desorbed ions had the same sign, positive or negative, depending upon the electrode polarity.

The invention described in this application stems from and relates to so called Electrospray (ES) ionization which can be considered a sort of mirror image of TS and AS in that instead of producing charging by atomization it produces atomization by charging. In ES the liquid sample is introduced through a small bore tube maintained at several kilovolts with respect to the surrounding walls of a chamber containing bath gas, usually but not necessarily at or near atmospheric pressure. The electrostatic field at the tip of the tube charges the surface of the emerging liquid. The resulting coulomb forces overcome the liquid's surface tension and disperse it into a fine spray of charged droplets. Thus, the nebulization is by electrostatic forces that provide a much higher charge/mass ratio for the resulting droplets than can be achieved in TS and AS. If the field at the tip of the tube is too high, or the pressure of the ambient bath gas is too low, a corona discharge will occur at the tip of the tube and substantially decrease the effectiveness of the nebulization. This ES ionization technique is fully described in U.S. Pat. Nos. 4,531,056 and 4,542,293 which were granted in 1985.

SUMMARY OF THE INVENTION

We have recently discovered that an ES source can produce ions from very large and complex solute species without any fragmentation. These species are so involatile that they could not possibly be convened intact into ions by ionization techniques such as EI, PI, CI or AI. Nor have there been reports that such large species have been ionized by either TS or AS. Moreover, and unexpectedly, it turns out that for species of large molecular weight the resulting ions each contain a large number of charges, distributed between a minimum and maximum number. The values of these minimum and maximum numbers depend on the size and composition of the species. For example, from protein solutes with molecular weights up to nearly 40,000 ions with up to 40 or more charges have been obtained. This multiplicity of charges reduces the mass/charge (m/z) ratio of the ions and, therefore, increases the effective mass range of any analyzer by a factor equal to the number of charges/ion. Thus, it was possible to analyze molecules having masses up to at least 40,000 daltons with a modest quadrupole mass filter whose nominal upper mass limit is 1500 daltons. The terms "effective" and "nominal" are used here to characterize the mass capability of an analyzer because conventional practice in mass spectrometry presumes that ions to be analyzed will almost always be singly charged. Consequently, in the m/z value for an ion, which is what analyzers measure, z has almost always been unity. Thus, an important feature of this invention was the discovery that with an ES ion source one could obtain useful mass spectra containing peaks corresponding to intact parent molecules, even though the molecular weight of those molecules was much higher than the nominal upper mass limit of the analyzer used to obtain the spectra. This remarkable result was entirely unexpected and had never been anticipated before this invention was reduced to practice.

Following the initial disclosure of our discovery (*Annual Meeting of the American Society for Mass Spectrometry* in San Francisco, 5–10 Jun. 1988) and using our methods, others have since produced protein ions with molecular weights as high as 130,000. (R. D. Smith, J. A. Loo, C. J. Barinaga and H. Udseth, presentation at the *5th (Montreux) Symposium on LC-MS,* Freiburg, November 1988). These large ions contain as many as 100 or more charges and their masses have been analyzed with a quadrupole mass spectrometer having a nominal mass range with an upper limit on the order of 1500 daltons. Moreover, this multiple charging phenomenon is not limited to ions having protein or protein-like structures. Multiply charged ions have also been produced by these methods from other large and complex molecules such as sugars, polynucleotides and synthetic polymers. For example, with an oligonucleotide having a molecular weight close to 4250, Covey, et al. obtained a mass spectrum with 6 peaks for parent ions containing from 6 to 11 negative charges. (T. R. Covey, R. F. Bonner, B. I. Shushan and S. D. Henion, Rapid. Commun. Mass Spectrom. 2,249 (1988)). A key requirement is that molecules that are not themselves ions contain polar atoms or groups, e.g. O, N, and S, to which the charge bearing species can attach, held presumably by ion induced dipole forces. Thus, molecules like hydrocarbons that are highly nonpolar cannot be effectively analyzed by the ES technique. The original experiments of Malcolm Dole and his colleagues (M. Dole, L. L. Mack, R. L. Hines, R. C. Mobley, L. D. Ferguson, and M. B. Alice, J. Chemical Physics, 49, 2240 (1968); see also 52, 4977 (1970)) seemed to show that ES could produce singly charged ions of large polystyrene polymers. However, convincing evidence has accumulated that the observed ions probably comprised clusters of polymer molecules with a plurality of charges on each cluster. These charged clusters probably represented residues of charged droplets after all the solvent had evaporated.

It is to be noted that ions comprising individual molecules with such high degrees of multiple charging are new to the laboratory. The classical ionization methods based on gas phase encounters between volatile molecules and electrons, photons or other ions, usually produce only singly charged ions but sometimes have provided ions with two charges and on rare occasions with three. Ions containing multiple charges have been produced by some of the recently developed "soft" ionization methods mentioned earlier such as TS, AS, FAB, SIMS and PD but usually with only two or three charges, never more than five or six. Moreover, a substantial fraction of the ions produced by these methods are singly charged, even for the very largest species. With ES ionization of species above some minimum size there are no detectable amounts of ions with less than some minimum number of charges. This minimum number of charges increases with increasing molecular weight of the parent species. For example, in the case of small proteins such as bovine insulin, lysozyme, and alcohol dehydrogenase, with respective molecular weights of 5,735, 14,306 and 39,830, the minimum numbers of charges were respectively 4, 10 and 32 in experiments under typical operating conditions. Traditionally, when peaks for doubly charged ions have been observed in a mass spectrum, mass spectrometrists have used them to confirm the assignment of a peak in that same spectrum to the molecular ion of the analyte. This assignment operation was fairly straightforward for two reasons: first, the molecular ion was singly charged, present in great abundance (since only the most stable molecules could form multiply charged ions) and had a mass that only rarely was outside the mass range of the analyzer; second, the multiple of the charge was almost always only two. This assignment technique is still used with PD where the multiplicity is still small, even very large ions having at most perhaps 2 to 5 charges. In some cases multiply charged ions have been regarded as a nuisance to be avoided because they were presumed to decrease the sensitivity of detection by robbing both analyte and charge from the primary peak (of singly charged ions) or because they might mask important fragments. Indeed, the initial reaction of mass spectrometrists, when confronted with a spectra containing a plurality of multiply charged parent peaks, has invariably been one of dismay. They instinctively feel that such peak plurality must inevitably decrease sensitivity and make interpretation of the spectrum much more difficult. A feature of this invention is that it turns into a substantial advantage this presumed disadvantage of multiplicity in numbers of peaks per spectrum and charges per ion. This advantage is especially real for situations in which the mass of the analyte species far exceeds the mass range of the mass analyzer. In such cases a peak for singly charged parent ions could not be observed in the spectrum, even if these ions were present in great abundance in the stream of ions entering the analyzer.

Another advantage of multiply charged ions, when they are produced in relatively high pressure gas that then carries them into the vacuum system by free jet expansion, is the narrow energy spread of the ions as they enter the mass analyzer. In order to promote evaporation of the droplets and desolvation of the ions it is often desirable to heat the bath gas to 350 K or so, a temperature well within the thermal stability limits of most organic and bio-organic compounds. During the adiabatic free jet expansion from the orifice into vacuum the bath gas temperature drops to values usually well below 100 K so that the internal degrees of freedom of the ions are quite cold when they enter the mass analyzer. The translational "temperature" of these ions as indicated by the density of the bath gas, or as measured by a thermometer moving with the gas at its same velocity, would be quite low, even somewhat lower than the "temperatures" of the internal degrees of freedom of either the ion itself or of the bath gas molecules. The reason is that these measures of temperature reflect primarily the translational energies of the ions and the molecules. The translational temperatures of any species in a gas undergoing rapid adiabatic expansion are always lower than the internal energies of those species. Thus the distribution of the ion translational energies is quite narrow, a substantial advantage for accurate mass analyses. Because heavy species (ions) are accelerated by the lighter carrier gas, the total translational energies (more properly "enthalpies") of the ions after expansion are higher than their thermal energies at the source temperature by a factor that is approximately equal to the ratio of the molecular weight of the ion to the mean molecular weight of the source gas, i.e. the concentration weighted average of the heavy species (ions) and the light species (bath gas). Thus, ions with a molecular weight of 100,000, at very low concentration in a bath gas of nitrogen expanded from a source temperature of 350 K, could in principle be accelerated to a translational kinetic energy of about 370 eV. That much energy in a singly charged ion as it entered a mass analyzer would complicate mass analysis because it would be too large for a quadrupole mass analyzer, for which acceptable inlet energies are much less than 370 eV. In addition, that much energy would constitute an appreciable but unknown fraction of the energy applied to an ion for mass analysis by time-of-flight or magnetic sector instruments. However, it has been well established that because of slip effects that result in a velocity lag for heavy species during acceleration by a much lighter carrier gas, the final velocity of such a heavy ion would probably be only 50 to 70 percent of the maximum bath gas velocity so that the translational energy of an ion with a molecular weight of 100,000 would be somewhere between 25 and 50 percent of the limiting value of 370 eV, i.e. less than 185 eV. Moreover, as will emerge, ions with molecular weights of 100,000 produced from an Electrospray source will generally have as many as 80 or more charges. Most mass analyzers respond to the ratio of kinetic energy or momentum to charge. Consequently, for example, an ion with 80 charges and a kinetic energy of 185 eV will behave in an analyzer like a singly charged ion with an energy of about 2.3 eV so that its mass analysis presents no difficulties.

A further advantage of this invention stems from a surprising finding in the ES ionization of large solute species that are pure compounds. With such substances, in which all molecules have the same molecular weight, the spectrum resulting from mass analysis of ions from an ES source comprises a sequence of peaks whose ions are multiply charged and differ from those of adjacent peaks by a single charge. In earlier experiments with polyethylene glycols (PEGs) we had observed ions with a multiplicity of charges. (S. F. Wong, C. K. Meng and J. B. Fenn, J. Phys. Chem. 92, 546 (1988)) However, because in every sample there was a broad range of oligomers, each of which could produce ions with varying numbers of charges, the spectra were so congested that we could only resolve individual peaks for ions with six charges or less. Moreover, even then the congestion made it impossible to discern whether a particular oligomer of given molecular weight gave rise to a coherent sequence of peaks in which the constituent ions of any one peak differed by a single charge from those of an adjacent peak. Indeed, the journal referees for that paper and another not yet published insisted that the relatively featureless band that was interpreted to represent multiply charged PEG oligomers was probably due to impurities. It was not until experiments described here had been carried out with proteins, each sample of which comprised mostly molecules that had essentially the same molecular weight (except for isotopic differences), that the remarkable coherent sequences of peaks that are an essential feature of our invention were discovered. Only after these protein results were revealed and interpreted did the mass spectrometry community accept the reality of such extensive multiple charging and the coherence of the resulting multiplicity of peaks in the mass spectra.

As this invention shows, when solutions containing a relatively small number of different solute species with relatively large molecular weights are introduced into an ES source, or any equivalent source that depends upon dispersing the solution to be analyzed into a bath gas as droplets that have a sufficiently high charge, the resulting ions constitute for each solute species a population in which each member consists of a molecule of that species to which are attached n charges. In that population n takes on all integral values between the maximum and minimum. Those minimum and maximum values are determined by the size and the composition of the species, both increasing as the species molecular weight increases. For the species studied to date the maximum number of charges seems to be such that the mass/charge (m/z) ratio of the ions is generally not less than about 500. Results also suggest that the minimum number of charges is such that the maximum value of m/z is probably under about 3000. For the large molecules of interest values this maximum value of m/z corresponds to values of n that are usually greater than 3 or 4.

A key difference between these ES ions and those produced by other soft methods, including FAB, PD, FIB, FD and LD, is that for most species with molecular weights above 3000 or so ions with values of n as low as 1 or 2 are absent altogether or constitute a very small fraction of the total population. In the other "soft" methods they are a significant component of the total ion population. These observations attest to substantial differences in the nature of the ionization process. It is believed that species with fewer than some minimum number of charges attached simply will not be desorbed from the droplet by the field existing at its surface. Thus, as species get larger the minimum number of charges required for "lift off" increases so that ions with fewer than that critical number are not found.

It has also been discovered, contrary to conventional mass spectrometry practice, that the multiplicity of peaks found in ES spectra is of great utility because it makes possible a significant enhancement of the confidence and accuracy with which one can assign a molecular weight to the parent species. Moreover, we have found convenient methods for achieving this enhancement and recovering information from mass spectra with such a multiplicity of peaks. Although these methods can be applied to any spectrum featuring multiple peaks due to multiple charging of a parent species, no matter how produced, they will be described with reference to mass spectra of ions produced in an Electrospray ion source that embodies principles that have been previously set forth in detail.

In sum, our invention relates to the production of mass spectra comprising a multiplicity of peaks, these peaks being produced by multiple charging of species with a relatively high molecular weight. It further relates to methods for the recovery of information from such spectra. An additional feature of the invention relates to the nature of the populations of multiply charged ions that we have been able to produce. They represent a new composition of matter. These features of the invention will be of particular value in the mass spectrometric analysis of samples containing complex and non-volatile species with molecular weights above about 3000. Other features and advantages of the invention will become apparent.

BRIEF DESCRIPTION OF THE DRAWINGS

The invention will now be set forth in greater detail by reference to the drawings in which:

FIGS. 9(A–E). Electrospray mass spectrum for a mixture of cytochrome C and myoglobin along with the deconvoluted spectrum for each species obtained by application of Equation 8.

DETAILED DESCRIPTION OF THE INVENTION

Figure 1:
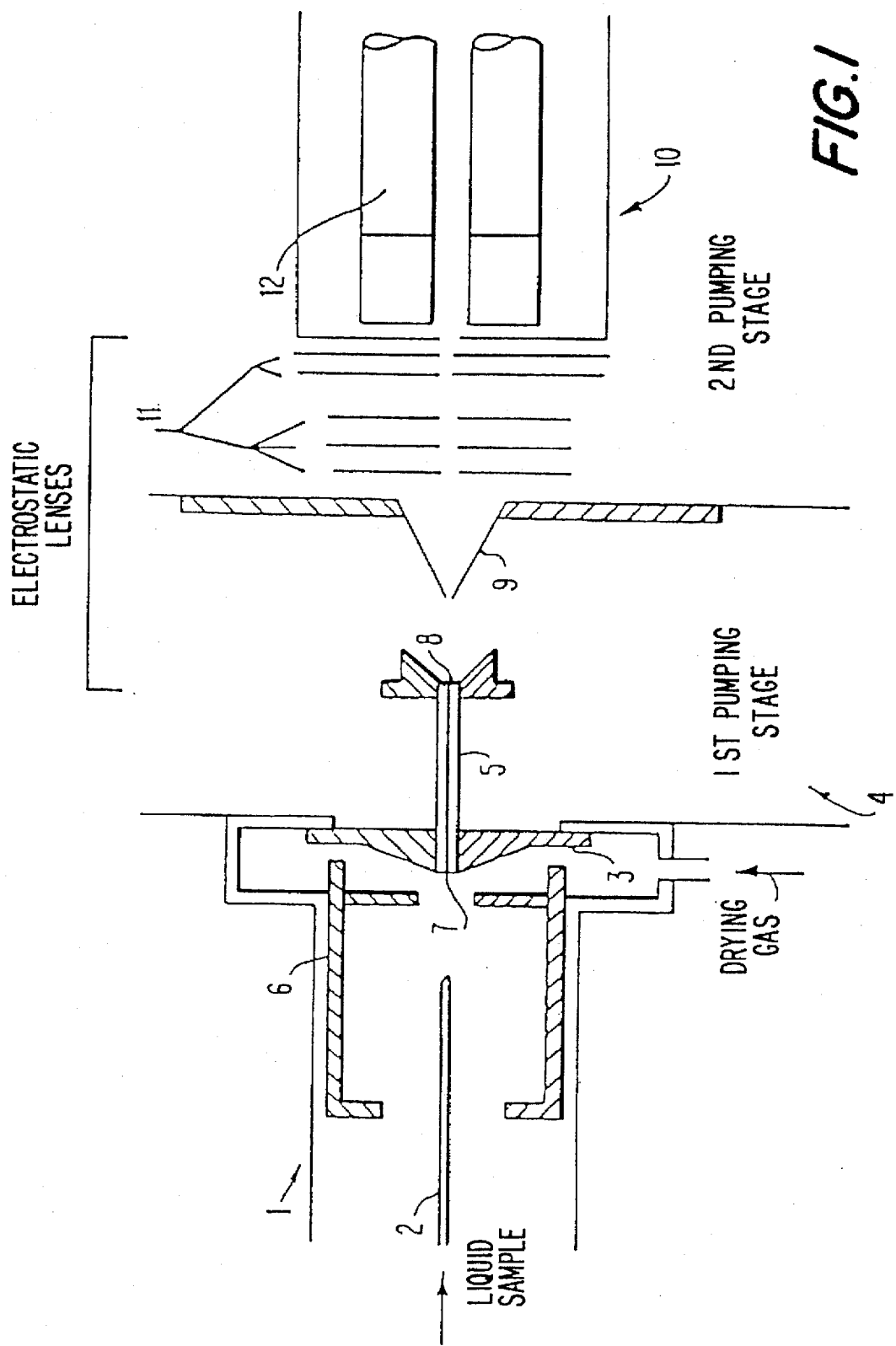
FIG. 1 is a simplified schematic representation of an apparatus with which the invention can be practiced.
Figure 2A:
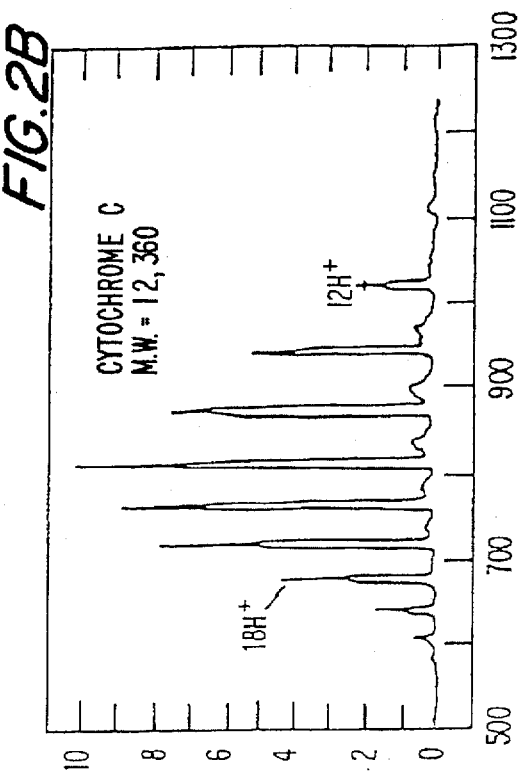
FIGS. 2(A–H) display mass spectra obtained for eight proteins with an apparatus that embodies the essential features schematically portrayed in FIG. 1. The number i of charges per constituent ion is indicated for representative peaks.
Figure 2B:
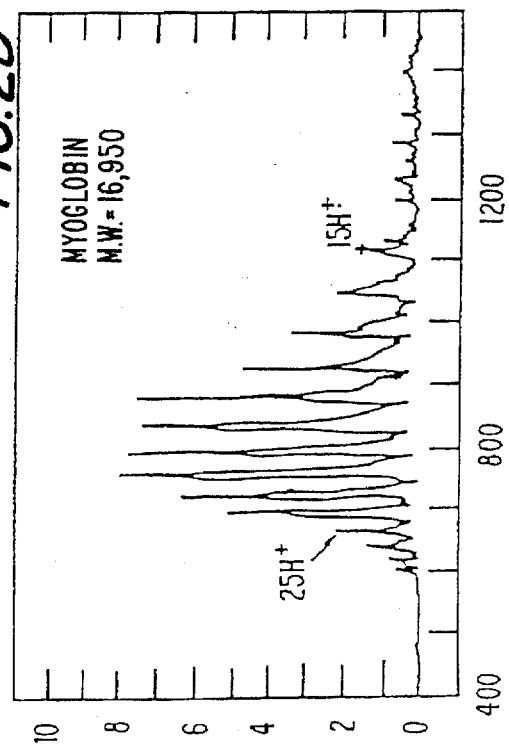
Figure 2C:
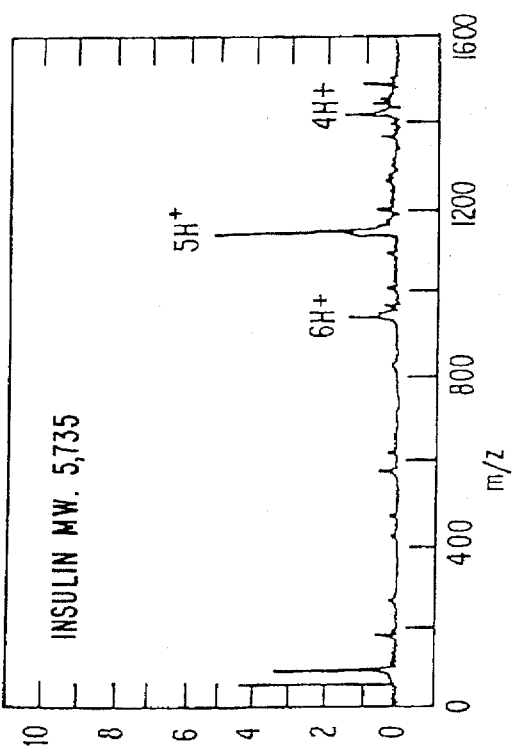
Figure 2D:
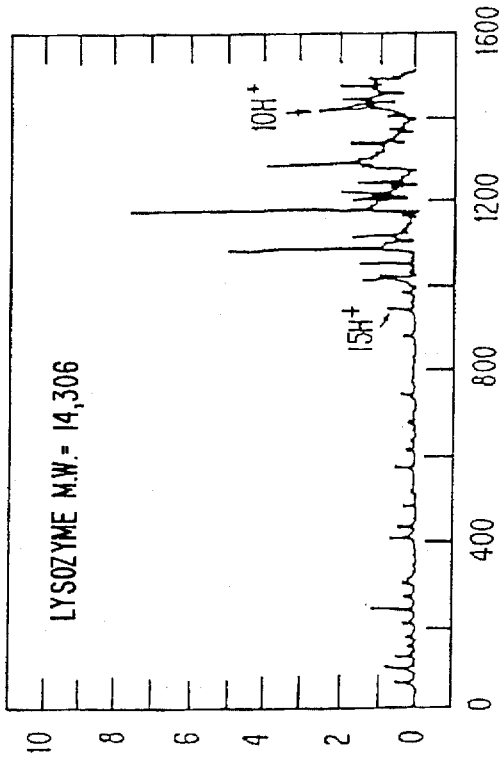
Figure 2E:
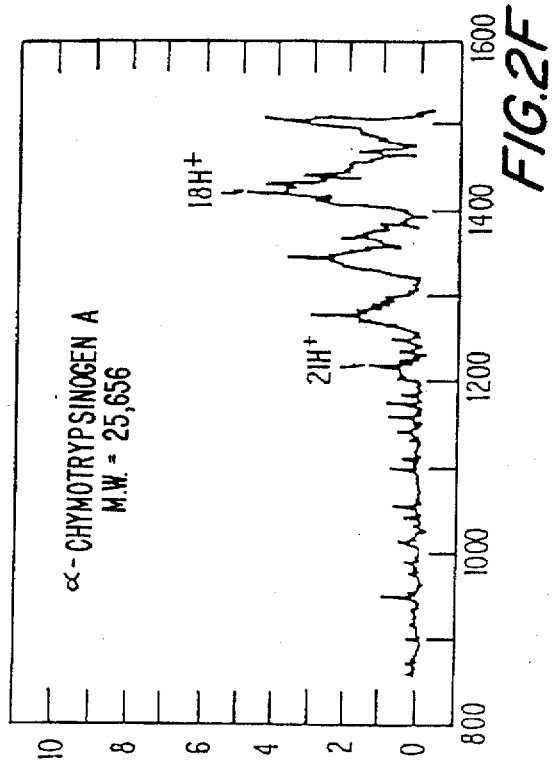
Figure 2F:
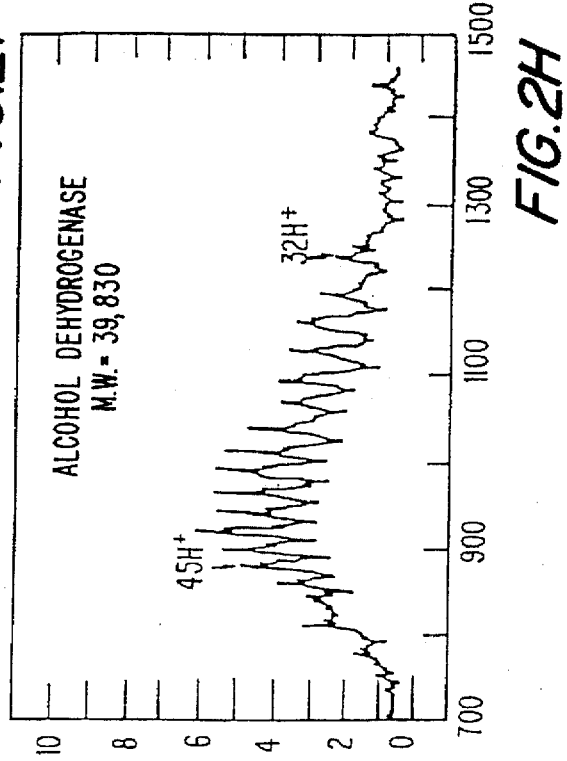
Figure 2G:
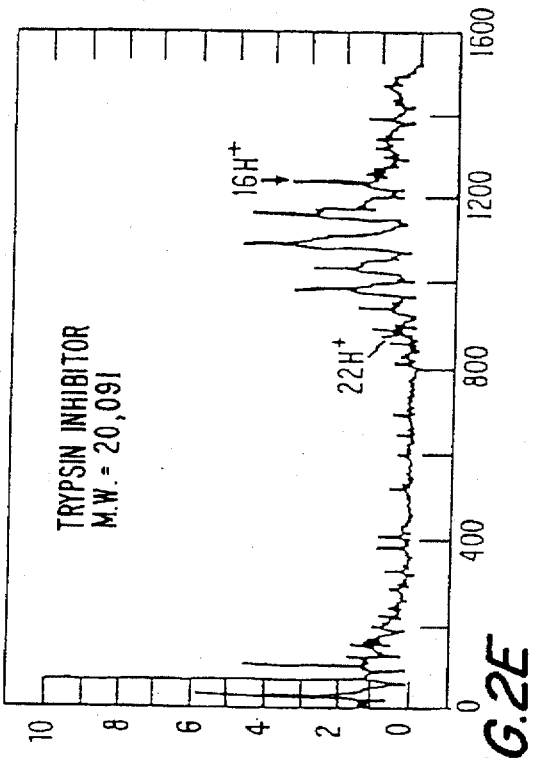
Figure 2H:
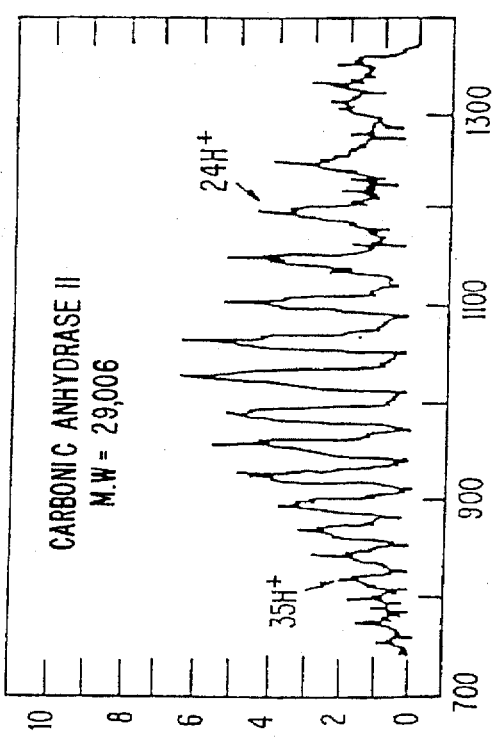

FIG. 1 shows a schematic representation of an apparatus in our laboratory that embodies the essential features of Electrospray Mass Spectrometry (ESMS) and has been described elsewhere. (C. M. Whimhouse, R. N. Dreyer, M. Yamashita, and J. B. Fenn, Anal. Chem. (1985) 57, 675; U.S. Pat. Nos. 4,531,056, (Labowsky, Fenn and Yamashita) and 4,542,293, (Fenn, Yamashita and Whitehouse). The following description of its operation also provides a convenient introduction to its principles. A solution containing the analyte at a flow rate usually between 1 and 40 µl/min enters the ES chamber 1 through a stainless steel hypodermic needle 2 maintained at a few kilovolts relative to the walls and end-plate 3. The most direct way to achieve this potential difference is to float the source of sample liquid, the hypodermic injection needle and the tube connecting them, at the required voltage while the rest of the apparatus is at or near ground potential. It is also possible to maintain the liquid injection needle at the required high potential, leaving the source of liquid sample at ground potential so that there is a voltage drop along the line between the two through which the sample liquid flows from source to needle. This voltage drop causes an electric current to flow from the needle, through the connecting tube to the source of liquid sample. The resulting current drain on the high voltage power supply can be minimized by making the connecting tube very long, thereby increasing its electrical resistance. Alternatively, a high voltage power supply can be installed that has sufficient capacity to maintain the desired voltage on the injection needle in spite of the current drain. In either of these cases the aperture leading into the vacuum system 4 can be a simple orifice or nozzle, but they both encounter problems of cost and safety. A more advantageous method of maintaining the source of sample liquid at ground potential, a most desirable operating condition when the sample source is a Liquid Chromatograph, is to replace the orifice with a capillary 5 of dielectric material, e.g. glass, as shown in FIG. 1. Satisfactory operation to produce positive ions can be then be obtained with the typical values of applied voltages indicated in parentheses after each of the following components: needle 2 (ground), surrounding cylindrical electrode 6 (−3500), metalized inlet 7 and exit 8 ends of the glass capillary (−4500 and +40 respectively), skimmer 9 (−20) through which a core portion of the ion-bearing gas from the free jet passes into a second vacuum chamber 10 containing ion lens 11 in front of the means of mass analysis 12 (ground). With this configuration, the source of liquid sample, the liquid sample injection needle 2 and the connecting tube, along with all external parts of the apparatus, are at ground potential and pose no hazard to an operator, as will be explained later.

To produce negative ions similar voltages of opposite sign are applied. In addition, it is useful to introduce a small stream of oxygen or other electron scavenger near the needle tip in order to inhibit the onset of a corona discharge which occurs at lower voltages in the negative ion mode. If the electrospray chamber is open to inspection the corona at the needle tip can be seen if the room is sufficiently dark and heard if it is sufficiently quiet. When the voltage is high enough to produce a corona in the positive mode the adduct cation in the spectral peaks very often becomes a proton, no matter what it was at lower voltages. In the negative ion mode the spectra sometimes contain peaks for ions to be expected if there is a discharge in a gas containing O, N and C, i.e. O—, NO—, CN—, $NO_2$—, OCN— and $O_2$—.

At first inspection the indicated potential difference of 4540 V between the inlet and exit ends of the capillary may seem startling. We have found that with the carrier bath-gas (nitrogen) at about one atmosphere the ion mobility is low enough so that the gas flow through the capillary can drag the ions out of the potential well at the capillary inlet and raise them back up to ground potential or as much as 15 kV above it. Thus, we can readily provide the energies necessary for injection into a magnetic sector analyzer. The capillary, with a bore of 0.2×70 ram, passes just about the same flux of both bath gas and ions as did the thin plate orifice (d=0, 1 mm) used in the original apparatus for producing the free jet "lock" between high and low pressure chambers in our first apparatus.

As the sample solution flows into the ES apparatus the field at the needle tip charges the surface of the emerging liquid which becomes dispersed by Coulomb forces into a fine spray of charged droplets. Driven by the electric field the droplets migrate toward the inlet end of the capillary through a countercurrent flow of bath gas typically at 800 torr, at an entering temperature from 320 to 350 K, and at a flow rate of about 100 mL/s. The optimum values of temperature and flow rate depend upon the design details of a particular apparatus, the species being analyzed and the objectives of the experiment. Flow rates of the bath gas that are too high may decrease sensitivity by preventing analyte ions with low mobilities from reaching the entrance to the capillary. If the flow rates are too low the extent of ion solvation may be excessive. However, in some cases it may be desirable to retain a certain amount of solvation in the ions by decreasing the bath gas temperature and/or the flow rate. Thus, while useable ion beams will be obtained with the bath gas parameters at what have been indicated as typical values, a certain amount of trial and error is advisable for determining the best flow rate and temperature for a particular experiment in a particular apparatus. The choice of bath gas is another important variable. The gas should be inert in the sense of not undergoing reaction or charge exchange with analyte ions. In addition it should have a relatively high dielectric strength in order to avoid breakdown and discharge at the tip of the injection needle even when the applied voltages are relatively high. It is also desirable that the gas should be inexpensive if the apparatus is to run for long periods of time. We have found that nitrogen is generally satisfactory. Carbon dioxide also works very well for many species. Air would serve if it is free of contaminants that might make chemical noise in the spectrum.

The solvent vapor from the evaporating droplets along with any other uncharged material are swept away from the capillary inlet by the bath gas flow. Meanwhile, in accordance with the scenario described earlier, the rapid evaporation of the migrating droplets promotes the sequence of Coulomb explosions that gives rise to droplets with a radius of curvature so small that the electric field at their surface is high enough to desorb solute ions into the ambient gas. Even solute species that are not themselves ions can attach solute cations or anions to their polar groups and desorb from the droplet as so-called "quasimolecular ions" suitable for mass analysis. Some of these desorbed ions are entrained in the flow of dry bath gas that enters the glass capillary to emerge at the exit end as a supersonic free jet in the first of two vacuum chambers. A core portion of this free jet passes through a skimmer into the second vacuum chamber, delivering ions to the mass analyzer. In the reduction to practice of this invention in our laboratory a quadrupole mass filter was used. However, the invention may be practiced with any kind of mass analyzer as long as the m/z values of the ions to be analyzed are within its range.

As noted earlier, ions produced by the ion sources traditionally used in mass spectrometry generally comprise singly charged species resulting from the loss or gain of an electron by a parent molecule. Thus the value of z is unity so that m/z, which is what analyzers measure, is numerically equal to the mass of the ion. Moreover, an appreciable fraction of the ions are often charged fragments of the parent molecule. On the other hand, ions produced by some of the more recently developed sources comprise neutral parent molecules to which small cations or anions are attached or from which protons or other charge bearing entities have been detached. These newer and "softer" ionization methods include those to which we have referred earlier: FAB, FIB, PD, LD, TS and AS. Due in part to the larger size of the parent molecules that can be accommodated by these sources and in part to the nature of their ionization processes, ions with up to five or six adduct charges have been observed. (P. Roepstorff and B. Sundqvist in "Mass Spectrometry in Biomedical Research," S. J. Gaskell, Ed., John Wiley, London, pp 269 ff (1986). However, such "extra" peaks have usually been unwelcome because they confuse the spectrum and are considered to "rob" intensity from the primary singly charged peak on which the determination of parent species mass is almost invariably based.

With the ES ion source shown in FIG. 1 mounted to a quadrupole mass spectrometer mass spectra for a number of proteins with molecular weights from 5000 to almost 40,000 daltons have been obtained. FIG. 2 shows some representative examples. Analoguous spectra have been obtained with other organic and bio-organic species including carbohydrates and oligo nucleotides. The analytical procedure involves dissolving the analyte samples in solvent or mixture of solvents. Solvent mixtures comprising acetonitrile, water and methanol or 1-propanol were most effective. It was advantageous in most analyses to lower the pH of the solution by addition of small quantities of acetic acid (HAC) or trifluoroacetic acid (TFA). The optimum proportions of these solvent components depended on the particular sample type and were determined by trial and error. Solutions with analyte concentrations ranging from 0.7 to 137 µmols/L, depending upon the species, were injected at flow rates of 8 µL/min. Similar spectra can be obtained with lower and higher flow rates. Flow rates as low as 1 µL/min and as high as 20 µL/min, even up to 40 µL/min in some cases have been utilized. At higher liquid flow rates, the spray tends to become unstable. It is possible however to maintain a reasonably stable spray at still higher flow rates if a flow of gas is used to "assist" the electrostatic dispersion of the liquid. However, such assistance always results in a lower charge/mass ratio for the droplets and in a decrease in sensitivity. In general, sensitivity increases as the liquid flow rate decreases because total ES ion current does not depend appreciably on flow rate so that the ratio of available charge to analyte mass increases as flow rate decreases. Each of the spectra shown in FIG. 2 is the result of a single scan requiring 30 seconds to cover the indicated mass range.

The essential features of each mass spectrum is shown in FIG. 2. It is immediately apparent from the mass spectrum that the extent of multiple charging in ES ionization is much larger than has been encountered with any other soft ionization method. For example, the ionization of bovine insulin by FAB (xenon at 8–10 KeV) produced only the singly and doubly charge molecular ion. (see e.g. Desidero and Katakuse, Biomed. Mass Spectrom., 1984, 11 (2), 55) This multiple charging feature of ES is very attractive in that it extends the effective mass range of any mass analyzer by a factor equal to the number of charges per ion. Moreover, because the multiply charged ions have lower m/z values, they are generally easier to detect and "weigh" than are the corresponding singly charged ions of the same specie. On the other hand, peak multiplicity distributes the signal for one species over several masses. For relatively large analyte molecules the number of charges per ion is almost always greater than the number of peaks. Therefore, the total current carried by one species is greater when there is peak multiplicity than would be the case for a single peak containing the same total number of singly charged ions. Unfortunately, the detector response per charge of a multiply charged ion is not known. It is known, however, that no post-acceleration has been required for multiply charged ions that were large enough to require such acceleration had they been singly charged. It is also known that the detection sensitivity obtained with ES ionization of large molecules seems to be substantially greater than has been obtained with sources giving rise to ions that are predominantly singly charged. Moreover, ion peak multiplicity allows multiple independent mass determinations from the data obtained in a single analytical procedure (i.e. mass scan). Such determinations can be averaged to provide mass assignments to the parent ion of large molecules with more precision and confidence than would be the case for a single peak of a singly charged ion. Two algorithms for achieving this improved method of mass determination, along with illustrative results obtained by applying them, will be set forth in what followings. One method of mass determination employs an averaging algorithm and the second employs a deconvolution algorithm. In all the calculations it is assumed that the detector response to any ion does not depend on the number of its charges. The application of the principles of this invention for the determination of the mass of large molecules are not limited to the described algorithm. Other algorithms and calculation methods for practicing the principle of the invention can be developed by those skilled in the art.

AVERAGING ALGORITHM

If one assumes that in a particular mass spectrum the adduct ions such as hydrogen, sodium etc. of each analyte all have the same identity, and therefore mass, and that any neutral adducts such as solvation species are the same for each ion, then there are three variables associated with each of the peaks in the series: the mass M (numerically equal to the relative molecular weight Mr) of the parent molecule including neutral adducts, the number of charges i, and the mass $m_a$ of the adduct ions. We use i rather than z to designate the number of charges in order to avoid confusion with the customary m/z scale of mass spectra for which m $=M+i\ m_a$, the total mass of the ion. In general $z=iq$ where q is an elementary charge and i is unity in conventional spectra for singly charged ions. It should be kept in mind that the units of m/z are properly daltons (Da) per elementary charge even though a measured peak position is often loosely expressed simply in daltons when z is one. All the formulas apply equally well to negatively charged ions with $m_a$ being negative in the case of charging by atom abstraction. Thus one can write for each of the peaks:

$$K_i = \frac{M + im_a}{i} = \frac{M}{i} + m_a \tag{1}$$

or $$(K_i - m_a) \equiv K'_i = \frac{M}{i}$$

where $K_i$ is the value of m/z for a peak position on the scale of the mass analyzer and $K'_i = K_i - m_a$ equals the m/z value of that peak position minus the adduct ion mass $m_a$. All masses are isotope averaged i.e., calculated using the chemical atomic weight scale. The positions of the peak maxima are used to determine the value of $K_i$. With the further constraint that i must be integral, equations 1 for any pair of peaks are in principle enough to determine the three unknowns simultaneously. Elementary manipulation of eqs. 1 for two charge states i and i+j (j>0) yields for the number of charges i:

$$i = j \frac{K'_{i+j}}{K'_i - K'_{i+j}} \quad (2)$$

For example, if the adduct ions are protons ($m_a=1$) and a peak at $K_i=1001.0$ and another one two peaks away ($j=2$) at $K_{i+2}=834.3$ are observed then $i=2$ $K+_{i+2}/(K'_i-K+_{i+2})=$ 1666.6/(1000−833.3)=10. That is, the peak at 1001 has 10 charges and the one at 834.3 has 12. The accuracy required in $K_i$ for determining i is low, especially if $K_i-K_{i+j}$ is made large, but increases as i gets larger. From eq. 2 it can be shown that an accuracy of one m/z unit in the determination of $K_i$ suffices for i's up to 100 or more i.e., a 100 kDa molecule if the average value of m/z is around 1000. Nor does the value of $m_a$ need to be exact for the determination of i because $m_a$ does not effect the denominator of eq. 2 and has only a small effect on the numerator. However, to determine the ion adduct mass directly from the peak positions we need a substantially higher accuracy in the measured values of $K_i$. From eqs. 1:

$$m_a = \frac{1}{j}((i+j)K_{i+j} - iK_i) \quad (3)$$

where i and i+j are for any two peaks. A measurement of $K_i$ with an accuracy of about $1/iK_i$ would be required to determine $m_a$ to within one dalton (i.e. an accuracy for Ki of approximately ±0.01 Da if $K_i=1000$ and M=10 kDa). However, a more modest mass accuracy will usually suffice because the possible values of $m_a$ are often well separated, e.g. $Na^+$ at 23 and $K^+$ at 39 Da. For proteins it is an assumed that $m_a=1$ which seems to be appropriate (at least as long as there is not too much sodium in the solution) and this assumption will be made in the numerical examples in this discussion.

With known charge number, and measured or assumed adduct ion mass $m_a$, the parent ion mass M can be obtained from any one peak or averaged from a number of peaks:

$$M = \frac{1}{n_o} \sum_i iK_i \quad (4)$$

where the summation is over the i values for the peaks selected for averaging and no is the number of those peaks.

The coherence of the peak sequence makes possible a further improvement in the estimate of M given by eq 4. This improvement allows us to identify and ignore peaks that do not belong in the sequence and to evaluate the quality of the spectrum. From eq 1 for any two peaks we obtain:

$$\frac{K'_i}{K'_{i+j}} = 1 + \frac{j}{i} \quad (5)$$

$$\frac{1}{i} = \frac{1}{j}\left(\frac{K'_i}{K'_{i+j}} - 1\right)$$

Figure 3A:
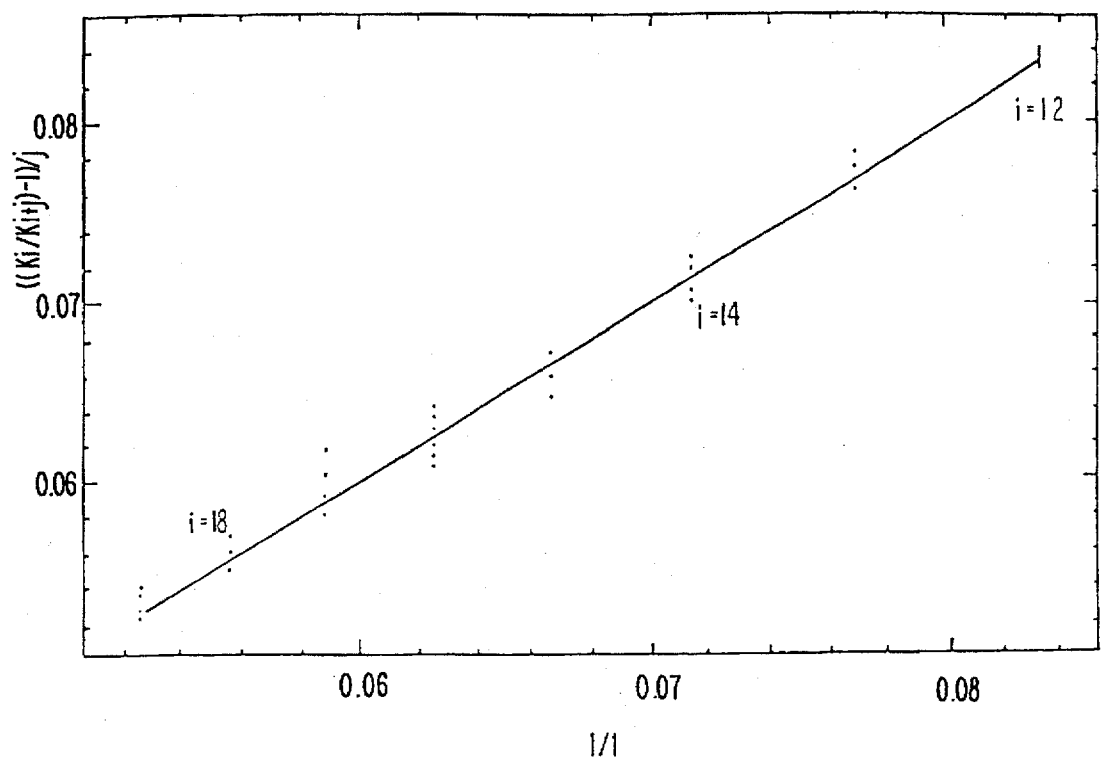
FIGS. 3(A–B) show a consistency check for the various peaks in the spectrum of the protein cyctochrome C shown in FIG. 2. The solid line is plot of Equation 5. The points are ratios of measured m/z values for different pairs of peaks (K'i/K'i+j), each for a different pair of peaks. In (a) the peak positions are as measured in the spectrum from FIG. 1. (b) same as (a) except that the peak for i=14 has been deliberately offset by 5 units on the m/z scale. The points representing peak ratios involving the offset peak are crosses.

Hence any pair of peaks in an experimental mass spectrum defines a point with $y=[(K'_i/K'_{i+j})-1]/j$ and $x=1/i$. All such points should fall on the line y=x. The scatter of the pair-points around this line is a measure of the quality of the mass spectrum. The more accurate the mass determination, the closer to the line the point will fall. FIG. 3a shows such a plot for the cytochrome C mass spectrum of FIG. 2. The seven points at each abscissa value of 1/i correspond to the seven possible ratios of $K'_i/K'_{i+j}$ for the eight peaks in the spectrum as i to i+j goes from 12 to 19. The quality of the experimental results can be readily inferred for each individual peak and for the mass spectrum as a whole from the departure of the points from the line values. The larger the spread around, or systematic offset from, the x=y line, the less reliable is the measurement. The sensitivity of this quality index is demonstrated in FIG. 3b. The points are from the same mass spectrum of cytochrome C, but the peak at i=14 was deliberately offset by 5 units of m/z. It is apparent that this "stray peak" can be readily distinguished from the sequence of peaks by the much larger spread about the line of all the points i=14 and of the cross points at the other values of i. The cross points represent pair combinations with the peak at i=14 when it was displaced by five m/z units. It should be pointed out that this plot is a test for self-consistency of the peaks in a sequence and does not depend on the value of parent mass.

The information on the quality of $K'_i$ values obtained from the above procedure can yield a better estimate of M by providing a weighting factor for each peak. In essence the contribution of each $K'_i$ in the averaging process is weighted in accordance with the proximity of its corresponding points to the straight line in a plot like the one in FIG. 3a. Equation 6 defines a relative weighting factor $w_i$ for each peak i:

$$w_i = \frac{(i_{max} - i_{min})}{W} \sum_{\substack{j=i_{min}-i \\ j \neq 0}}^{i_{max}-i} \left( \frac{\left|\frac{i}{i+j} - \frac{K'_{i+j}}{K'_i}\right|}{\frac{i}{i+j}} \right)^p \quad (6)$$

where $$W = \sum_{i_{min}}^{i_{max}} w_i$$

Figure 3B:
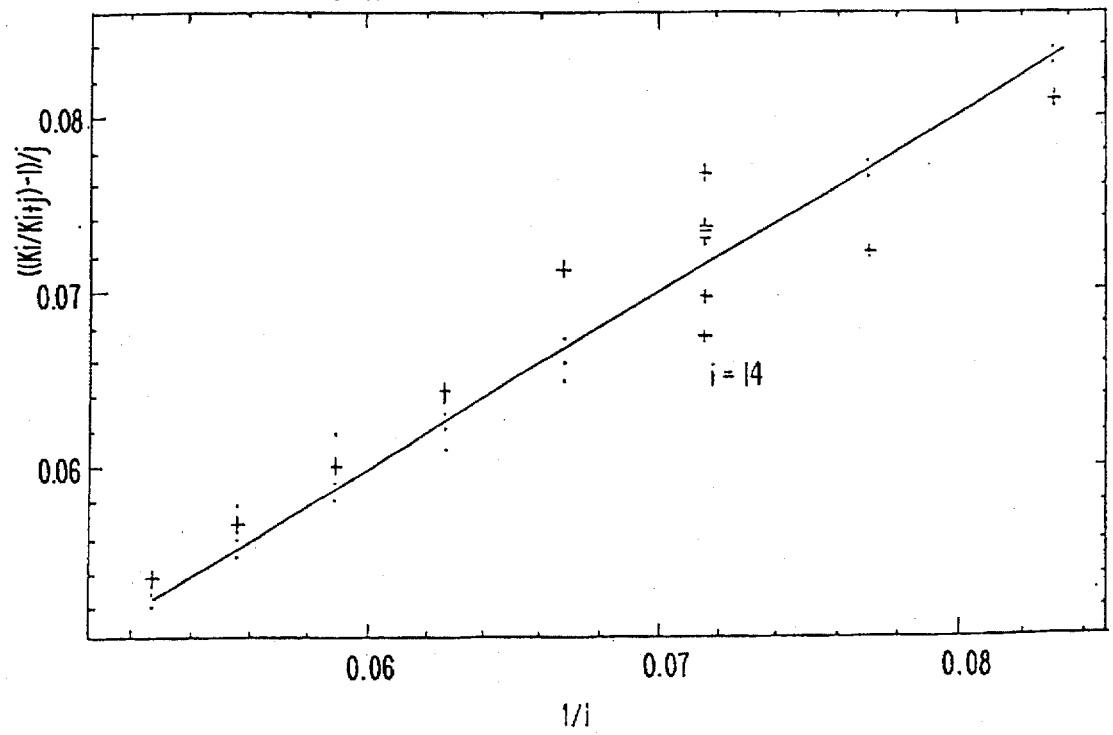
Figure 4:
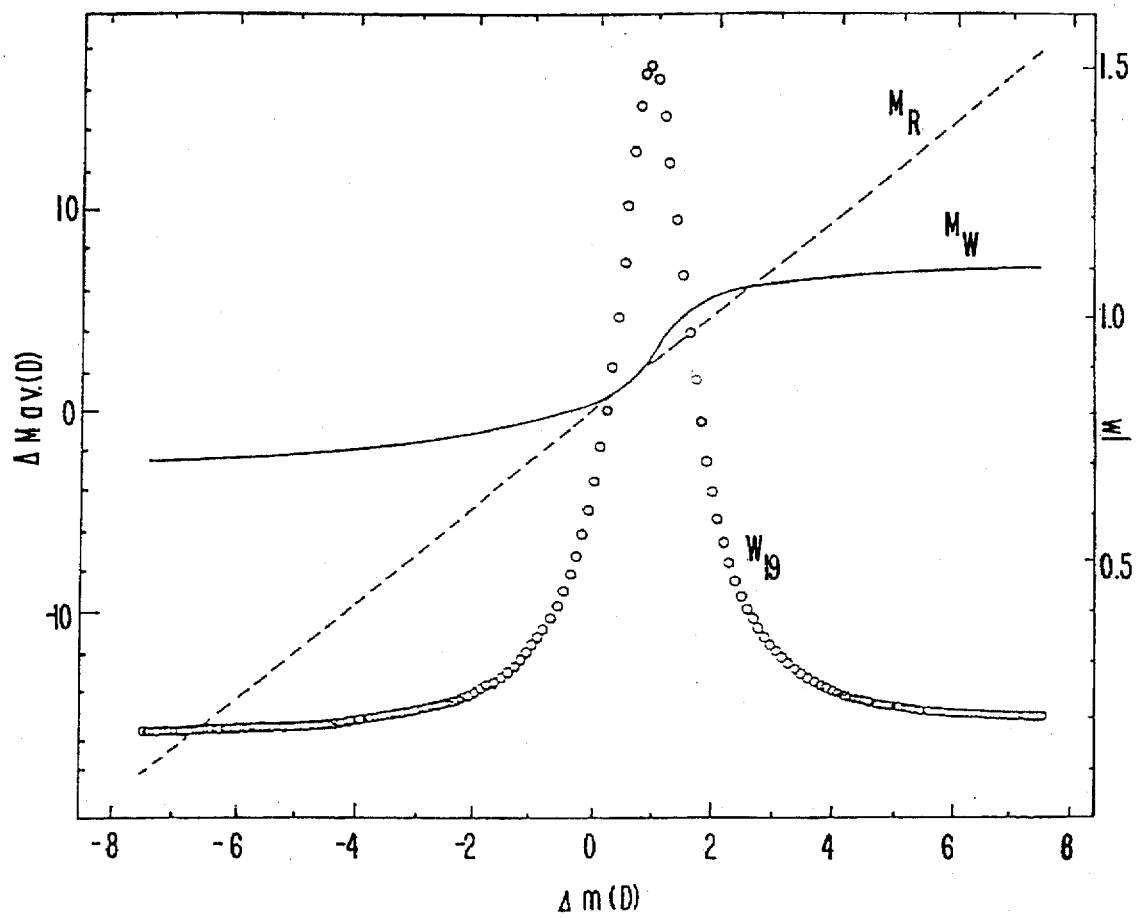
FIG. 4 shows the result of offsetting m/z for the i=19 peak by an amount m in the mass spectrum for cyctochrome C. The dashed line shows the effect on the unweighted average mass, the solid line on the weighted mass. Note that the weighted average is much less affected by the offset peak once that peak is away from its "best position" with respect to the rest of the peaks in the sequence. The open circles represent (on the right hand ordinate) the relative weighting factor $w_{19}$ when p=2.

W is the normalizing constant and p is an integer equal to or greater than 2 which specifies the dependence of w on the proximity of the parent point to the straight line in FIG. 3b. For a peak whose $K'_i$ has a better than average fit into the sequence pattern, $w_i$ tends to be greater than one. It tends to be less than one if the $K'_i$ value departs from its "ideal" position by an amount greater than the average of all the other peaks. The larger its departure the smaller will be its weighting factor and its relative contribution to the overall average. FIG. 4 shows how the unweighted average differs in behavior from the weighted average obtained with $w_i$'s from eq. 6 for p=2. To produce FIG. 4, the peak at i=19 in the cytochrome C spectrum (FIG. 2) was shifted in increments from −7.5 to +7.5 units from its measured m/z value and at every position we calculated the relative weighting factor $w_{19}$, the unweighted average, and the weighted average with a value of 2 for p. Evidently a shift of −7.5 mass units in $K'_{19}$ results in a unweighted mass average shift of −17.8 mass units whereas the weighted average shifts by just −2.6 mass units, only 15% of the mass shift in the unweighted case. The location of the maximum in $w_{19}$ indicates that the measured $K'_{19}$ was one unit too low according to the other peaks of the sequence, corresponding to an error somewhat larger than the standard deviation of ±5 Da in the final mass determination for cytochrome C. Choosing a value for p greater than 2 further enhances the dependence of the weighting factor $w_i$ on the deviation of peak $K'_i$ from the ideal m/z value. The decrease in the weighted standard deviation $s_w$, which is calculated by multiplying by $w_i$ the contributions of each $K'_i$ to the error, becomes smaller as p increases. For the case of carbonic anhydrase II (M=29,006): $s_w$ decreases from ±15.6 mass units for the unweighted average to ±7.9 mass units for p=6. It should be noted that the weighted average does not necessarily change monotonically as p is increased.

In comparing the parent mass obtained by this weighting procedure with the true mass one has to keep in mind that there are at least two sources of error that contribute to ΔM (i.e. $M_{true}-M_{meas}$). One, the statistical error in ascertaining the individual peak positions, is expressed in the unweighted or weighted standard deviation of the measured mass M. The other arises from systematic errors in the calibration of the analyzer mass scale. This latter source of error will obviously not be affected by any weighting procedure. If the error due to mass calibration predominates, weighting the average will not provide a major improvement in mass accuracy. In such a case the standard deviations, weighted or unweighted, do not indicate the experimental accuracy of a measurement but only its precision. A criterion for deciding if mass scale calibration is negligible in determining the error in M is:

$$i_{(ave)}\Delta Da \ll s \tag{7}$$

where $i_{ave}$ is an average number of charges per ion in the sequence of peaks, s is the standard deviation derived from averaging the individual peaks, and ΔDa is the absolute value of the error in daltons of the mass scale calibration. For the example of the cytochrome C spectrum ($i_{ave}$=15, s=±5 Da, ΔDa≈1 Da) the criterion is not fulfilled and the overall error is dominated by ΔDa. Hence in these measurements we would not expect a major decrease in ΔM from the weighting procedure.

Calculating the weighting factors $w_i$ allows a judgement of the quality of a spectrum in much the same way as does noting the scatter of points in a plot like the one in FIG. 3a. In the plot a misassigned peak can be identified by a large difference between y and x values of points in a plot like the one in FIG. 3b. Large differences correspond to low $w_i$ values in the numerical procedure of eq 6.

The accuracy with which mass assignments can be made depends directly on the accuracy of the analyzer's mass scale. For unit mass accuracy at 100 kDa the scale error must be smaller than 0.01 m/z units (eq 7). If mass scale calibration is not a problem (i.e. if eq 7 is satisfied, for example, by peak matching) and the values of $K'_i$ could be determined to within 0.1 mass units, then unit mass accuracy up to masses of several tens of kilodaltons might be possible even for quadrupole instruments (cf. eq 4 with $i_{ave}$=50 and $n_o$=25). Of course, this calculation presupposes that the $K'_i$ values can be determined as accurately for high mass molecules with multiple charges as they can be for singly charged low mass molecules.

It should be noted that isotope spread does not contribute appreciably to peak broadening. The contribution to peak half-width from the isotope distribution in a typical protein even at 100 kDa ($C_{4590}$ $H_{6720}$ $N_{1260}$ $O_{1500}$ $S_{30}$, i.e. a scaled-up version of Glucagon) is less than 30 mass units (8). The corresponding spread in m/z is less than 0.3 mass units in a peak for ions with 100 charges, not an unreasonable number for such a large molecule.

DECONVOLUTION ALGORITHM

Visual interpretation of a spectrum comprising multiply charged peaks, and determination of parent mass, would be simplified if the coherent sequence of peaks could be transformed to one singly charged peak located on an m/z scale at the molecular mass M of the parent compound. It will be shown that the following function can provide such a transformation:

$$F(M^*) = \sum_{i=1}^{\infty} f\left(\frac{M^*}{i} + m_a\right) \tag{8}$$

Figure 5A:
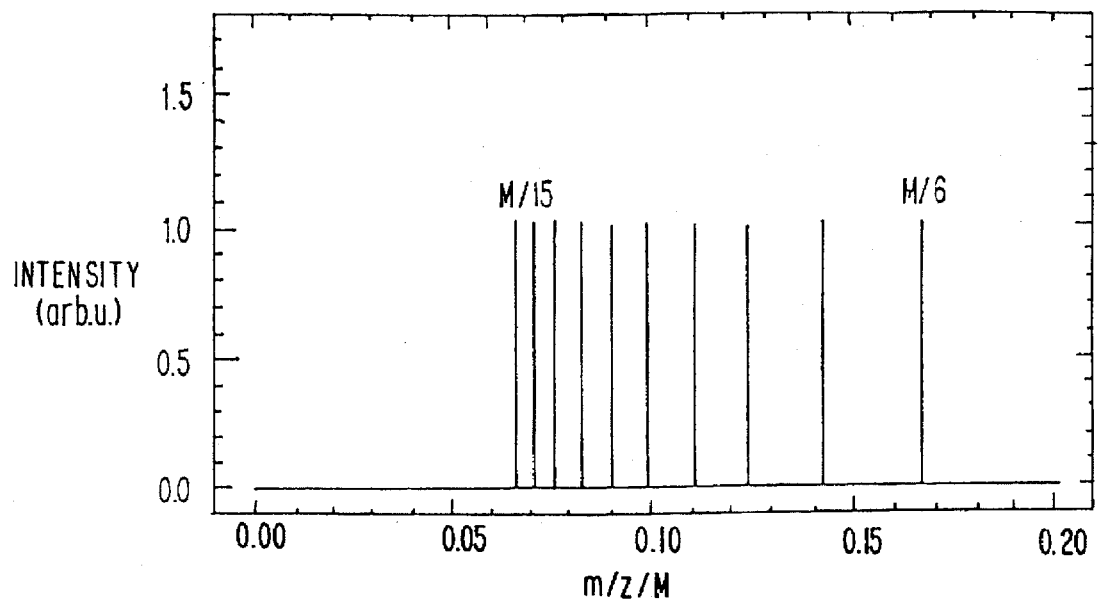
FIGS. 5(A–B) (a) A synthetic sequence of peaks for ions with from 6 to 15 charges. (b) Deconvolution of (a) by Equation 8. The mass scale is in units of the parent mass M.

F is the transformation function for which the argument M* is any arbitrarily chosen trial value of M for which F is to be evaluated. The symbol f represents the distribution function for peak heights in a measured mass spectrum. For example, if there is a peak of relative intensity 5 at m/z=500 then f(500)=5. $m_a$ is the adduct ion mass, as previously defined. It will be shown below that the function F has its maximum value when M* equals the actual value of M, the parent mass of the multiply charged ions in the sequence. Thus, evaluating F at all values of M* with $0 \leq M^* \leq \infty$ yields a transformed or "deconvoluted" spectrum, in which the peak with maximum height corresponds to the parent species with a single massless charge. An example will make it clear how the deconvolution algorithm reconstructs the parent peak from the sequence. For simplicity we assume $m_a$=0. FIG. 5a shows a hypothetical measured spectrum f generated by charging a molecule with mass M with from 6 to 15 massless adduct ions such that the height is unity for every peak in the sequence. These "measured" peaks occur at M/6, M/7, ... M/15. If F is evaluated at M*=M the following sum is obtained:

$$F(M) = f\left(\frac{M}{1}\right) + f\left(\frac{M}{2}\right) + \ldots + f\left(\frac{M}{5}\right) + f\left(\frac{M}{6}\right) + \ldots + f\left(\frac{M}{15}\right) + f\left(\frac{M}{16}\right) + f\left(\frac{M}{17}\right) + \ldots$$
$$= 0+0+\ldots+0+1+\ldots+1+0+0+\ldots = 10$$

Thus, the function F has created a peak at the position M*=M with a height equal to the sum of the heights of the sequence peaks. It is assumed that the height of any peak in a measured spectrum is related to the abundance of its ions by the same proportionality constant no matter how many charges are on those ions.

If F is evaluated at M+ε, a position slightly larger than M, then F will be zero because (M+ε) does not correspond to the position of any of the sequence peaks. However, it is also apparent from the example that the function F will create peaks in the deconvoluted spectrum at more positions than at M*=M. At M*=2/3M the following sum results:

$$F\left(\frac{2M}{3}\right) = f\left(\frac{\left(\frac{2M}{3}\right)}{1}\right) + f\left(\frac{\left(\frac{2M}{3}\right)}{2}\right) + \ldots =$$
$$f\left(\frac{M}{6}\right) + f\left(\frac{M}{9}\right) + f\left(\frac{M}{12}\right) + f\left(\frac{M}{15}\right) = 4$$

Figure 5B:
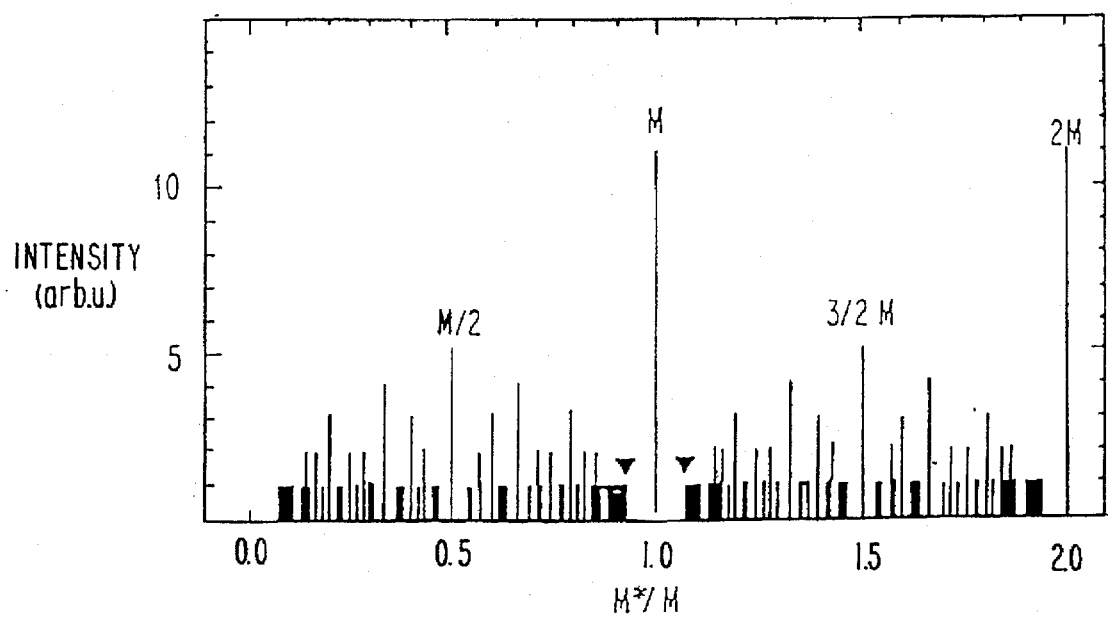

FIG. 5b shows the results of applying eq. 8 to the spectrum of FIG. 5a, an ideal sequence of multiply charged ions with $6 \leq i \leq 15$. It is a property of the spectrum resulting from the transformation F, as shown in FIG. 5b, that it comprises a series of calculated peaks containing contributions from the actual peaks in an observed spectrum. By reference to the above procedure, a number of general features of the deconvoluted spectrum can be inferred. As we have already noted, its most prominent peak occurs when M* equals the parent mass M and has a magnitude equal to the sum of the magnitudes of the individual peaks in the sequence. The next highest peak occurs at M/2 and it is at most only half as high as the peak at M. In general there are peaks at (k/i) M, where $i_{min} \leq i \leq i_{max}$ and k is any integer. In the sequence of "side peaks" on either side of the parent peak those closest to the parent (maximum) peak M occur at $((i_{max} \pm 1)/i_{max})$ M where $i_{max}$ is the highest number of charges on a single ion. The position of these closest side peaks is indicated by arrowheads in FIG. 5b. The height of these side peaks is a factor of $1/(i_{max}-i_{min})$ smaller than the height of the molecular peak at mass M. The deconvoluted spectrum is periodic in M. This periodicity may be viewed physically as being due to synthetic "overtones" of the basic spectrum corresponding to doubling, tripling etc., of both the parent mass and the number of charges on each peak, and a difference of 2, 3 etc. in the i values of adjacent peaks.

Figure 6A:
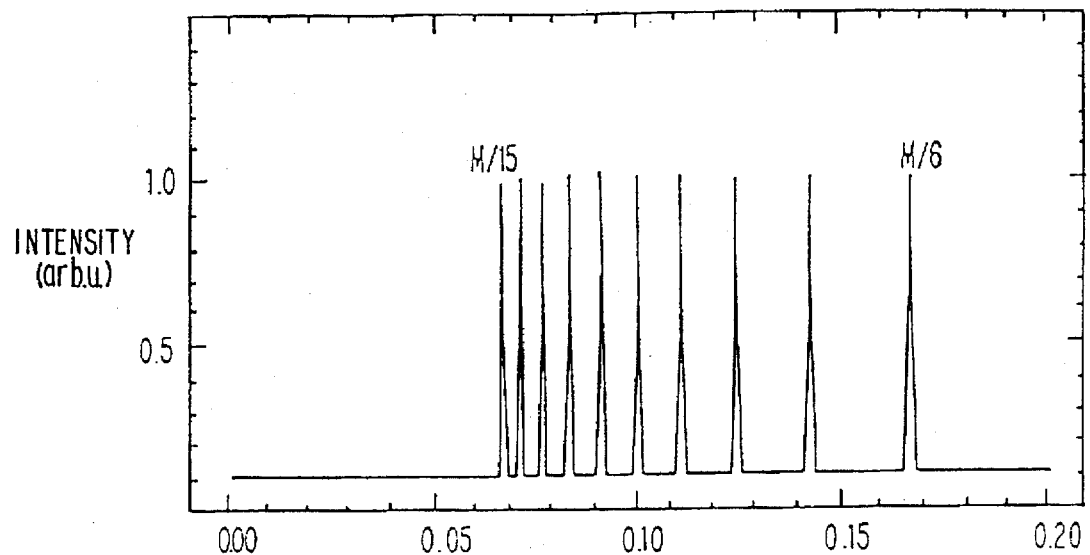
FIGS. 6(A–B) (a) Synthetic sequence of peaks whose shapes are approximated by isosceles triangles (FWHH= 0.5%) A constant background contribution that is 10% of the peak height has been incorporated. (b) Transformation of (a) according to Equation 8.
Figure 6B:
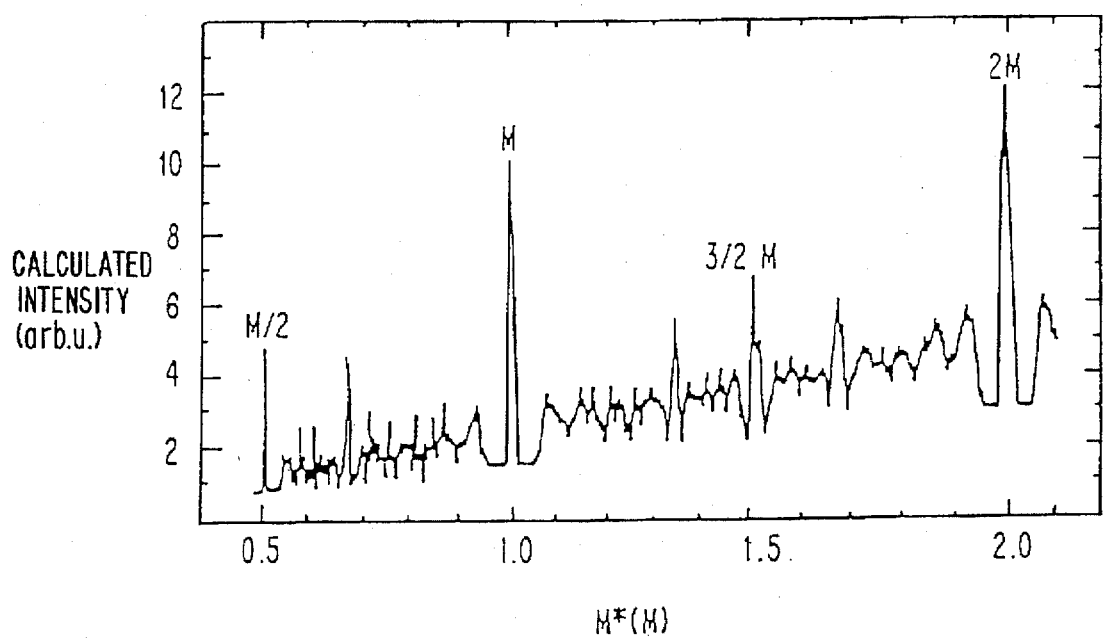

The transformed spectrum changes somewhat in appearance if finite resolution and background are taken into account. To simulate these effects, the shapes of individual peaks in the sequence of FIG. 5a are represented in FIG. 6a by isosceles triangles with a relative full width at half height (FWHH) of 0.005. Furthermore, a constant background of 10% of the peak height was introduced. The consequences of this treatment are seen in FIG. 6b. There is a progressive increase in the magnitude of the "side peaks" because the non-zero peak width in the observed spectrum results in a contribution to F at m/z values on either side of the peak centers. The steady increase in the "baseline" is caused by more frequent sampling of the background at higher values of M*.

Figure 7A:
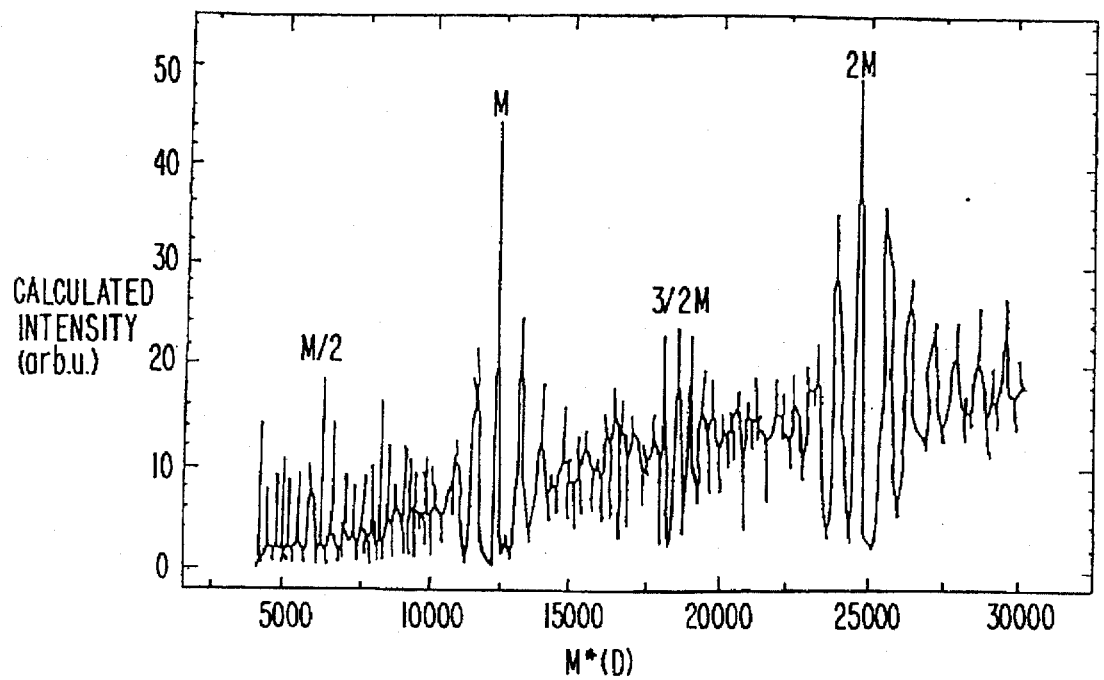
FIGS. 7(A–B) (a) Deconvolution by Equation 8 of the spectrum for cytochrome C (M=12,260) in FIG. 2. The theoretical positions of the first side peaks are marked by dark triangles. (b) "zoom" expansion of the spectrum in (a) for the mass range between 10,000 and 14,000. See text for explanation of the peak marked by the open triangle.
Figure 7B:
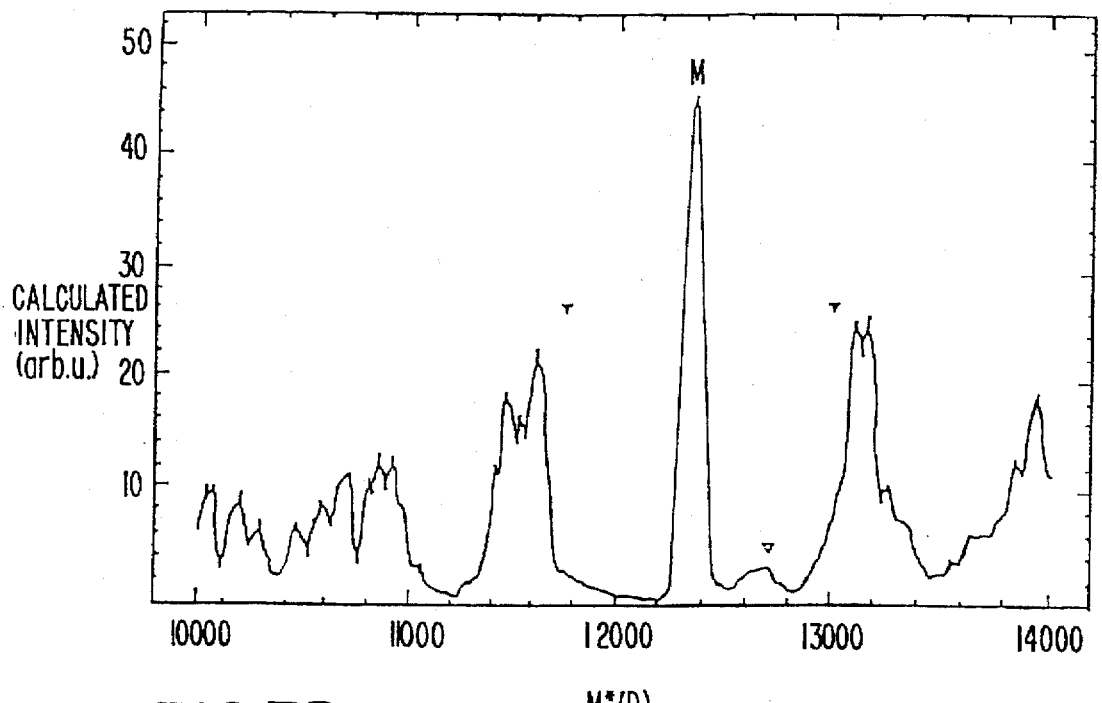
Figure 8A:
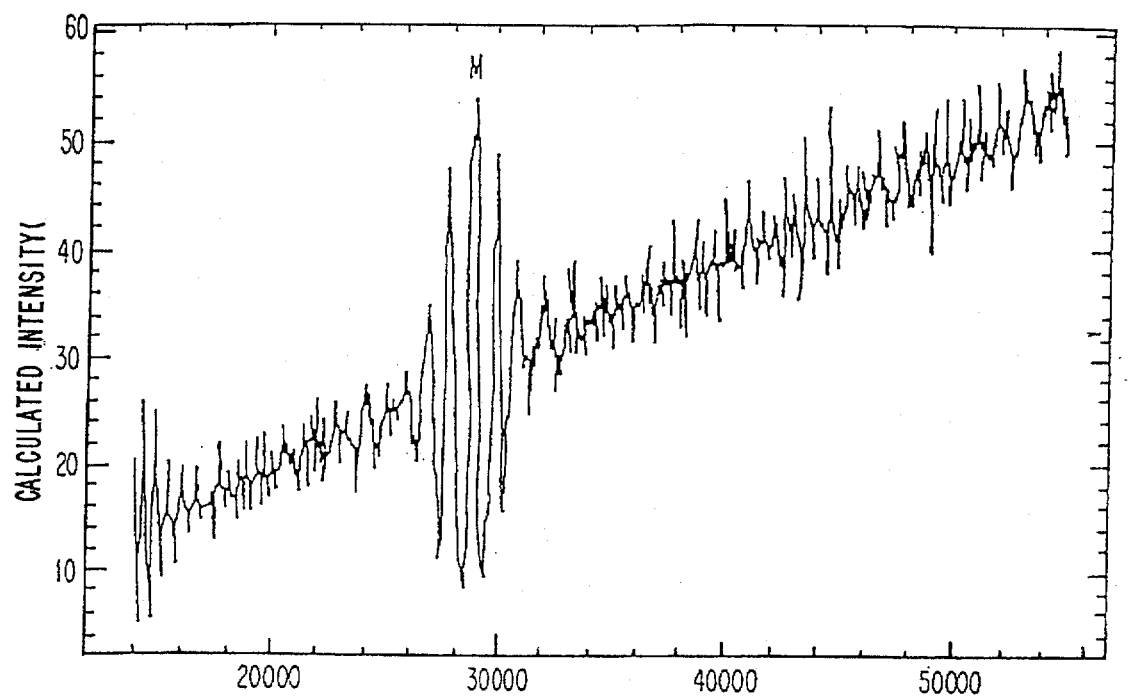
FIGS. 8(A–B). Result as in FIG. 7 of applying the deconvolution algorithm to the spectrum in FIG. 2 for carbonic anhydrase II (M=29,006).
Figure 8B:
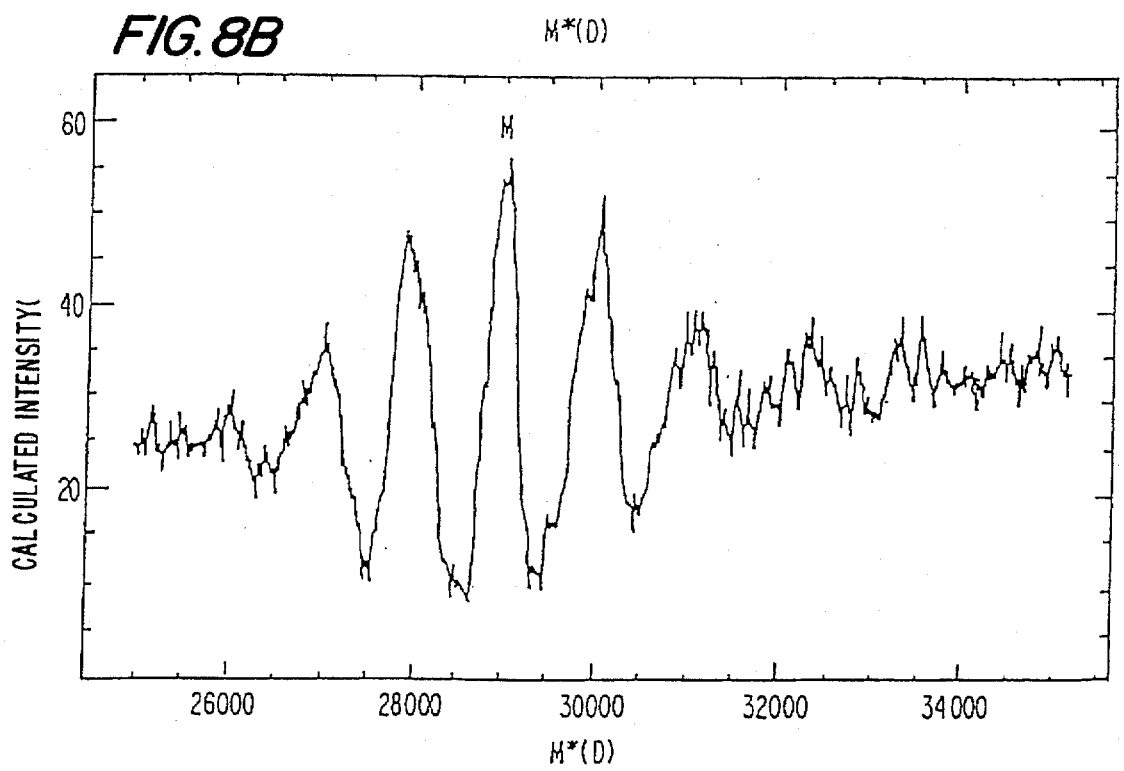

This "deconvolution algorithm" was applied to the eight experimental spectra shown in FIG. 2 with the assumption that $m_a=1$. Each mass spectrum was represented by 1150 data points for a full seam in the algorithm a linear interpolation between adjacent data points was used. It should be pointed out that the algorithm needs no a priori information about charge states or the number of peaks in the sequence. The only instruction specific to a particular spectrum is the range of m/z in the "window" that spans the peaks to be deconvoluted. Thus the summation of eq. 8 goes only from the minimum to the maximum values of m/z within this window. Such a limitation in the range of the summation reduces the noise in the transformed spectrum because background signal that lies outside the range of interest is not sampled. FIG. 7a displays the result of applying the deconvolution procedure to the mass spectrum of cytochrome C in FIG. 2. The transformed spectrum clearly shows the side peaks, the overtone periodicity and the baseline increase discussed above. The parent (largest) peak is magnified in FIG. 7b by "zoom" expansion of the mass scale in its vicinity. FIG. 8 shows the results of the same treatment for the case of a larger protein, carbonic anhydrase II (M=29,006 Da). Widths at half maximum for both measured and deconvoluted peaks for the other spectra were usually about 1%. Such large spreads resulted in part because effective resolution of the mass analyzer used to collect these mass spectra was only about 300.

In general there is a region immediately around the parent peak that is free from artifacts of the deconvolution algorithm. As noted above, this region should extend from $(i_{max}-1)/i_{max} \times M$ to $(i_{max}+1)/i_{max} \times M$, where $i_{max}$ is the maximum number of charges found on a molecule. In FIGS. 5 and 6 the boundaries of this region are marked by black triangles. In the deconvoluted cytochrome C mass spectrum (FIG. 7), however, a small peak (marked with an open triangle) is observed about 340 mass units higher than the molecular peak. Detailed examination of the measured spectrum reveals a small peak just above each main peak in the sequence whose position agrees with the peak found in the deconvolution. This observation indicates that the algorithm can readily detect small peaks close to a parent peak that may be due, for example, to parent species variants with slightly different masses.

This method for the determination of the mass of large molecules can also be applied when two or more parent species are present in the sample. FIG. 9 shows the mass spectrum for a solution of cytochrome C and myoglobin, each at a concentration of 0.5 mg/ml in an acidified mixture of acetonitrile, methanol and water. Also shown is the result of applying the deconvolution algorithm along with a "zoom" magnification of the pertinent parts of the deconvoluted spectrum. As might be expected, the number of different species that a mixture can contain and still be resolved by this procedure depends upon their relative concentration in the mixture and difference in their masses. The key factor is how close together are the peaks of the component multiply charged ions and whether the available analyzer can resolve them.

We claim:

1. A composition of matter comprising a population of multiply charged polyatomic ions derived from a distinct polyatomic parent molecular species, all molecules of said distinct polyatomic parent molecular species having substantially the same molecular weight and chemical identity, the number of charges on each ion in said population of multiply charged polyatomic ions defining that ion's charge state number, said population of multiply charged polyatomic ions comprising a plurality of sub-populations of ions, all the ions of each of said sub-populations having the same charge state number, said same charge state number differing from the charge state numbers of the ions in the other sub-populations of said plurality of subpopulations, said plurality of sub-populations comprising one sub-population for each value of charge state number beginning with a smallest value not less than three and extending to a largest value not less than five.

2. The composition of matter of claim 1 in which said smallest value of charge state number is not less than five and said largest value is not less than seven.

3. The composition of matter of claim 1 in which said smallest value of charge state number is not less than seven and said largest value is not less than ten.

4. The composition of matter of claim 1 in which said population of multiply charged polyatomic ions is formed by:
   dispersing a solution containing said one or more distinct polyatomic parent molecular species into a bath gas as charged droplets, said dispersing taking place in the presence of an electric field; and
   allowing the solvent of said solution to evaporate from said charged droplets until at least some molecules of said distinct polyatomic parent molecular species become dispersed in said bath gas as said multiply charged polyatomic ions.

5. The composition of matter of claim 1 in which said polyatomic parent molecular species is selected from a class of compounds known as biopolymers.

6. The composition of matter of claim 1 in which said distinct polyatomic parent molecular species is not a synthetic polymers such as a poly (ethylene glycol), having less than four different constituent elemental species.

7. The composition of matter of claim 1 such that a mass analysis of said multiply charged polyatomic ions in said population of multiply charged polyatomic ions comprising a plurality of sub-populations, produces a set of values for the mass/charge ratios of the multiply charged polyatomic ions in said population of ions, said set of values of mass/charge ratios providing a basis for calculating a value of molecular weight for the said polyatomic parent molecular species from which said population of multiply charged polyatomic ions is formed.

8. The composition of matter as claimed in claim 1 in which said distinct polyatomic parent molecular species has a molecular weight not less than 5000.

9. A composition of matter comprising one or more populations of multiply charged polyatomic ions derived from a sample comprising at least one polyatomic parent molecular species, the number of charges on each ion defining said ion's charge state number, said population of multiply charged polyatomic ions formed from said at least one polyatomic parent molecular species comprising a plurality of sub-populations, the ions of each sub-population having the same charge state number, said charge state number differing by one from the next largest and the next smallest values of charge state number found in the other sub-populations of said plurality, the ions of each of said sub-populations having a value of said charge state number that is not less than five, said composition of matter being formed by:

dispersing a solution of said sample containing said at least one polyatomic parent molecular species into a bath gas as charged droplets, said dispersing taking place in the presence of an electric field; and allowing the solvent of said solution to evaporate from said charged droplets until at least some molecules of said polyatomic parent molecular species become dispersed in said bath gas as said multiply charged polyatomic ions.

10. The composition of matter of claim 9 in which the charge state number of the ions in each of said sub-populations of said plurality of sub-populations is at least seven.

11. The composition of matter of claim 9 in which all molecules of said at least one of said polyatomic parent molecular species have substantially the same molecular weight.

12. The composition of matter of claim 9 in which said single polyatomic parent molecular species is selected from the class of compounds known gas biopolymers.

13. The composition of matter of claim 9 such that when a mass spectrum is generated from said population of multiply charged polyatomic ions, an analysis of the mass/charge values of the ions giving rise to each of said peaks in said sequence of peaks in said mass spectrum leads to a value of the molecular weight of said single polyatomic parent molecular species.

14. The composition of matter of claim 13 in which said sizable polyatomic parent molecular species has a molecular weight not less than 5000.

15. The composition of matter of claim 9 in which said single polyatomic parent molecular species has a molecular weight of not less than about 5000.

16. A composition of matter comprising one or more distinct populations of multiply charged polyatomic ions generated from a sample comprising one or more distinct polyatomic parent molecular species, the number of charges on each ion defining the ion's charge state number, each of said populations of polyatomic ions comprising a plurality of sub-populations, each of said plurality of sub-populations being comprised of ions formed from one of said distinct polyatomic parent molecular species and having the same charge state number, there being at least one of said populations of multiply charged polyatomic ions that comprises one of said sub-populations for each value of charge state number beginning with a smallest value of three and extending to a largest value not less than five.

17. The composition of matter of claim 16 in which said smallest value of charge state number is not less than five and said largest value of charge state number is not less than seven.

18. The composition of matter of claim 16 in which said smallest value of charge state number is not less than seven and said largest value of charge state number is not less than ten.

19. The composition of matter of claim 16 in which all molecules of each of said distinct polyatomic parent molecular species have substantially the same molecular weight.

20. The composition of matter in claim 16 in which at least one of said distinct polyatomic parent molecular species is selected from a class of compounds known as biopolymers.

21. The composition of matter in claim 16 in which at least one of said distinct polyatomic parent molecular species is selected from the group comprising proteins, peptides, polypeptides, carbohydrates, oligonucleotides and glycoproteins.

22. The composition of matter of claim 16 in which at least one of said distinct polyatomic parent molecular species is not a synthetic polymer, such as a poly (ethylene glycol), having less than four different constituent elemental species.

23. The composition of matter of claim 16 in which at least one of said distinct polyatomic parent molecular species has a molecular weight not less than about 5000.

24. A composition of matter comprising one or more distinct populations of multiply charged polyatomic ions generated from a sample comprising one or more distinct polyatomic parent molecular species, the number of charges on each ion defining its charge state number, each of said populations of multiply charged polyatomic ions comprising ions formed from one of said distinct polyatomic molecular species and being comprised of a plurality of sub-populations, the ions of each of said sub-populations having the same charge state number, there being one of said sub-populations for each value of said charge state number beginning with a smallest value not less than three and extending to a largest value not less than five.

25. The composition of matter of claim 24 in which said smallest value of charge state number is at least five and said largest value is not less than seven.

26. The composition of matter of claim 24 in which at least one of said distinct polyatomic parent molecular species is selected from a class of compounds known as biopolymers.

27. The composition of matter of claim 24 in which at least one of said distinct polyatomic parent molecular species is selected from the group comprising proteins, peptides polypeptides, carbohydrates, oligonucleotides and glycoproteins.

28. The composition of matter of claim 24 in which at least one of said distinct polyatomic parent molecular species is not selected from the group comprising synthetic polymers having less than four different constituent elemental species, said group comprising poly (ethylene glycol)s.

29. The composition of matter of claim 24 in which at least one of said distinct polyatomic parent molecular species has a molecular weight not less than 5000.

30. The composition of matter of claim 24 in which at least one of said distinct polyatomic parent molecular species has a molecular weight not less than 7000.

31. A composition of matter comprising one or more distinct populations of multiply charged polyatomic ions generated from a sample comprising one or more distinct polyatomic parent molecular species, the number of charges on each ion defining the ion's charge state number, each of said populations of multiply charged polyatomic ions comprising ions formed from one of said distinct polyatomic parent molecular species in said sampler at least one of said populations of multiply charged polyatomic ions being comprised of a plurality of sub-populations, the ions of each of said sub-populations having the same value of charge state number, that value being different from the values of charge state number in all the other sub-populations of ions in said plurality of sub-populations, the smallest value of charge state number of the ions in said plurality of sub-populations being not less than three, said composition of matter being formed by:

dispersing a solution containing said one or more distinct polyatomic parent molecular species into a bath gas as charged droplets, said dispersing taking place in the presence of an electric field.

allowing the solvent of said solution to evaporate from said charged droplets until at least some molecules of said distinct polyatomic parent molecular species become dispersed in said bath gas as said multiply charged ions.

32. The composition of matter of claim 31 in which said smallest value of charge state number is not less than five.

33. The composition of matter of claim 31 in which said smallest value of charge state number is not less than seven.

34. The composition of matter of claim 31 in which all molecules of any one of said distinct polyatomic parent molecular species have substantially the same molecular weight.

35. The composition of matter of claim 31 in which all molecules of at least one of said distinct polyatomic parent molecular species have the same chemical formula.

36. The composition of matter of claim 31 in which all molecules of each of said distinct polyatomic parent molecular species are chemically indistinguishable.

37. The composition of matter of claim 31 in which at least one of said distinct polyatomic parent molecular species is selected from the class of compounds known as biopolymers.

38. The composition of matter of claim 31 in which at least one of said distinct polyatomic parent molecular species is not selected from the group of synthetic polymers having less than four different constituent elemental species, said group comprising poly (ethylene glycol)s.

39. The composition of matter of claim 31 in which at least one of said distinct polyatomic parent molecular species has a molecular weight not less than about 5000.

40. The composition of matter of claim 31 in which said bath gas is heated.

41. The composition of matter of claim 31 in which said bath gas flows in a direction substantially counter current to the direction in which said charged droplets drift in said electric field.

42. The composition of matter of claim 31 in which said bath gas is at approximately atmospheric pressure.

43. A composition of matter comprising one or more populations of multiply charged polyatomic ions generated from a sample comprising one or more distinct polyatomic parent molecular species, the number of charges on each ion defining the ion's charge state number, each of said populations of multiply charged polyatomic ions comprising ions formed from one of said one or more distinct polyatomic parent molecular species, at least one of said populations of ions comprising a plurality of sub-populations of ions, all the ions in each sub-population having the same charge state number, said at least one of said populations comprising one such sub-population for each possible value of charge state number beginning with a smallest value not less than three and extending to a largest value not less than five, said composition of matter being useful in the determination of a value of molecular weight for one or more of said distinct polyatomic parent molecular species, said determination of molecular weight being achieved by means of a mass analysis of ions from said one or more populations of ions and a calculation of the molecular weight values of said one or more polyatomic parent molecular species from the values of mass/charge (m/z) obtained by said mass analysis for the ions in said one or more populations of polyatomic ions.

44. The composition of matter of claim 43 in which said smallest value of charge state number is not less than five and said largest value of charge state number is not less than seven.

45. The composition of matter of claim 43 in which said smallest value of charge state number is not less than seven and said largest value of charge state number is not less than ten.

46. The composition of matter of claim 43 in which all molecules of any particular one of said distinct polyatomic parent molecular species have substantially the same molecular weight.

47. The composition of matter of claim 43 in which at least one of said distinct polyatomic parent molecular species is selected from a class of compounds known as biopolymers.

48. The composition of matter of claim 43 in which at least one of said distinct polyatomic parent molecular species is selected from the group comprising proteins, peptides, polypeptides, carbohydrates, oligonucleotides and glycoproteins.

49. The composition of matter of claim 43 in which at lease one of said distinct polyatomic parent molecular species is not selected from the group of synthetic polymers having less than four different distinct elemental constituent species, said group comprising poly (ethylene glycol)s.

50. The composition of matter of claim 43 in which at least one of said distinct polyatomic parent molecular species has a molecular weight not less than 5000.

51. The composition of matter comprising one or more populations of multiply charged polyatomic ions generated from a sample comprising one or more distinct polyatomic parent molecular species, the number of charges on each ion defining the ion's charge state number, each of said populations comprising ions formed from one of said one or more distinct polyatomic parent molecular species, at least one of said populations of multiply charged polyatomic ions comprising a plurality of sub-populations of ions, all the ions in each sub-population having the same charge state number, said same charge state number differing from the charge state numbers of the ion in the other sub-populations of said population, said charge state number having a value of at least five for all the ions in said at least one of said populations of multiply charged polyatomic ions, said composition of matter being useful for determining the molecular weight of one or more of said distinct polyatomic parent molecular species, said determination of the molecular weight being achieved by a mass analysis of the ions in said one or more populations of multiply charged polyatomic ions together with a calculation of the said molecular weight of said one or more polyatomic parent molecular species from the values of mass/charge (m/z) obtained by mass analysis of ions in said one or more populations of multiply charged polyatomic ions.

52. The composition of matter of claim 51 in which every ion in said at least one of said populations of multiply charged polyatomic ions has a charge state number not less than seven.

53. The composition of matter of claim 51 in which at least one of said distinct polyatomic parent molecular species is selected from a class of compounds known as biopolymers.

54. The composition of matter of claim 51 in which at least one of said distinct polyatomic parent molecular species is selected from the group comprising proteins, peptides, polypeptides, carbohydrates, oligonucleotides and glycoproteins.

55. The composition of matter of claim 51 in which at least one of said distinct polyatomic parent molecular species is not selected from the group comprising poly (ethylene glycol)s.

56. The composition of matter of claim 51 in which at least one of said distinct polyatomic parent molecular species has a molecular weight not less than 5000.

57. A composition of matter comprising one or more distinct populations of multiply charged polyatomic ions generated from a sample comprising one or more distinct polyatomic parent molecular species, the number of charges on each ion defining the ion's charge state number, each of said multiply charged polyatomic ions in any one of said one or more distinct populations having been formed from one of said distinct polyatomic parent molecular species in said sample, at least one of said distinct populations of multiply charged polyatomic ions comprising a plurality of sub-populations of ions, all the ions in each sub-population of said plurality of sub-populations having the same charge state number, said same charge state number differing from the charge state numbers of the ions in the other sub-populations of said plurality of sub-populations, said plurality of sub-populations comprising one such sub-population for each possible value of charge state number beginning with a smallest value not less than three and extending to a largest value not less than five, said composition of matter being formed by:
dispersing a solution containing said polyatomic parent molecular species into a bath gas as charged droplets, said dispersing taking place in the presence of an electric field;
allowing the solvent of said solution to evaporate from said charged droplets until at least some molecules of said distinct polyatomic parent molecular species become dispersed in said bath gas as said multiply charged polyatomic ions;
said composition of matter having the property that the molecular weight of each of said distinct polyatomic parent molecular species in said sample can be calculated from the mass/charge (m/z) values of the multiply charged polyatomic ions produced from that species.

58. The composition of matter of claim 51 in which said smallest value of charge state number is not less than five and said largest value is not less than seven.

59. The composition of matter of claim 51 in which said smallest value of charge state number is not less than seven and said largest value is not less than ten.

60. The composition of matter of claim 51 in which all molecules of any particular one of said distinct polyatomic parent molecular species have substantially the same molecular weight.

61. The composition of matter of claim 51 in which at least one of said distinct polyatomic parent molecular species is selected from the class of compounds known as biopolymers.

62. The composition of matter of claim 51 in which at least one of said distinct polyatomic parent molecular species is selected from the group comprising proteins, peptides, polypeptides, carbohydrates, oligonucleotides and glycoproteins.

63. The composition of matter of claim 51 in which at least one of said distinct polyatomic parent molecular species is not selected from the group of synthetic polymers comprising less than four different constituent elemental species, said group comprising poly (ethylene glycol)s.

64. The composition of matter of claim 51 in which at least one of said distinct polyatomic species has a molecular weight not less than 5000.

65. The composition of matter of claim 51 in which said bath gas is heated.

66. The composition of matter of claim 51 in which said bath gas flows in a direction substantially counter current to the direction of drift of said charged droplets in said electric field.

67. The composition of matter of claim 51 in which said bath gas is at approximately atmospheric pressure.

68. A composition of matter that by mass analysis of its component ions is found to comprise one or more distinct populations of multiply charged polyatomic ions, the number of charges on each ion defining the ion's charge state number, each of said distinct populations of multiply charged polyatomic ions comprising ions having been formed from a polyatomic parent molecular species, at least one of said distinct populations of multiply charged polyatomic ions comprising a plurality of sub-populations of ions, all the ions in each sub-population having the same charge state number, said charge state number differing from the charge state number of the other sub-populations in said plurality of sub-populations, said plurality of sub-populations comprising one such sub-population for each possible value of charge state number beginning with a smallest value not less than three and extending to a largest value not less than five, said composition of matter being formed by:
dispersing a solution containing one or more polyatomic molecular species into a bath gas as charged droplets, said dispersing taking place in the presence of an electric field;
allowing the solvent of said solution to evaporate from said charged droplets until at least some molecules of said polyatomic parent molecular species become dispersed in said bath gas as said multiply charged polyatomic ions;
said mass analysis being carried out on a portion of said multiply charged polyatomic ions in said bath gas that is introduced into a vacuum system containing a mass analyzer.

69. The composition of matter of claim 68 in which said smallest value of charge state number is not less than five and said largest value is not less than seven.

70. The composition of matter of claim 68 in which said smallest value of charge state number is not less than seven and said largest value is not less than ten.

71. The composition of matter of claim 68 in which all molecules of any one of said distinct polyatomic parent molecular species in said solution have the same chemical identity.

72. The composition of matter of claim 68 in which at least one of said distinct polyatomic parent molecular species in said solution is selected from a class of compounds known as biopolymers.

73. The composition of matter of claim 68 in which at least one of said distinct polyatomic parent molecular species in said solution has a molecular weight not less than 5000.

74. A composition of matter derived from a sample comprising one or more distinct polyatomic parent molecular species, all molecules of each of said distinct polyatomic parent molecular species having substantially the same molecular weight and chemical identity, said composition of matter comprising one or more distinct populations of polyatomic ions, at least one of said distinct populations of ions comprising multiply charged ions formed from one of said one or more distinct polyatomic parent molecular species in said sample, the number of charges on each ion defining the charge state number of that ion, each of said populations of multiply charged ions having the property that when its ions are mass analyzed they give rise to a mass spectrum comprising a multiplicity of peaks, said multiplicity of peaks comprising at least one coherent sequence of peaks, the ions of each peak in said coherent sequence having the same charge state number, said charge state number being greater thorn unity and differing by one unit from the charge state numbers of the ions of each immediately adjacent peak in said coherent sequence, said coherent sequence comprising one peak for each different value of charge state number beginning with a smallest value not less than three and extending to a largest value not less than five.

75. The composition of matter of claim 74 in which said smallest value of charge state number is not less than five and said largest value of charge state number is not less than seven.

76. The composition of matter of claim 74 in which at least one of said distinct polyatomic parent molecular species is selected from a class of compounds known as biopolymers.

77. The composition of matter of claim 74 in which at least one of said distinct polyatomic parent molecular species is not selected from the group comprising poly (ethylene glycol)s.

78. The composition of matter of claim 74 in which at least one of said distinct polyatomic parent molecular species has a molecular weight not less than about 5000.

79. The composition of matter of claim 74 in which at least one of said distinct polyatomic parent molecular species has a molecular weight not less than 7000.

80. A composition of matter comprising one or more distinct populations of multiply charged polyatomic ions, each of said multiply charged polyatomic ions in said distinct populations being characterized by the symbol xi, the numerical value of xi being the m/z value of said one of said multiply charged ions such that xi=Mr/i+ma wherein Mr is the molecular weight of a distinct parent polyatomic molecular species from which all of said multiply charged polyatomic ions in said distinct population of multiply charged polyatomic ions are derived, i is an integer equal to the number of adduct charges attached to a molecule of said distinct polyatomic parent molecular species to form one of said multiply charged polyatomic ions, ma is the effective average mass (which can sometimes be negative) of each said adduct charge, each of said distinct populations of multiply charged polyatomic ions comprising a plurality of sub-populations, the ions of each sub-population having the same values for i, ma and Mr and therefore the same value of xi, said distinct populations of ions including at least one population in which all the ions have values of i greater than two.

81. The composition of matter of claim 80 in which said one or more distinct populations of multiply charged polyatomic ions include at least one population in which all the ions have values of i greater than three.

82. The composition of matter of claim 80 in which said one or more distinct populations of multiply charged polyatomic ions include at least one population in which all the ions have values of i greater than five.

83. The composition of matter of claim 80 in which at least one of said polyatomic parent molecular species selected from a class of compounds known as biopolymers.

84. The composition of matter of claim 80 in which at least one of distinct polyatomic parent molecular species is selected from the group comprising proteins, peptides polypeptides, carbohydrates, oligonucleotides and glycoproteins.

85. The composition of matter of claim 80 in which at least one of said distinct polyatomic parent molecular species is not selected from the group comprising poly (ethylene glycol)s.

86. The composition of matter of claim 80 in which the mass spectrum of said distinct populations of multiply charged polyatomic ions comprises a coherent sequence of peaks in which the ions of each peak differ from the ions of immediately adjacent peaks by one adduct charge, the set of mass/charge (m/z) values for the ions of the peaks in said coherent sequence leading by appropriate calculations to a value for the molecular weight (Mr) of the distinct parent polyatomic molecular species from which are formed the polyatomic ions whose mass spectrum comprises said coherent sequence of peaks.

87. The composition of matter of claim 80 in which at least one of said distinct polyatomic parent molecular species has a value for said molecular weight (Mr) not less than 5000.

88. The composition of matter of claim 80 in which at least one of said distinct polyatomic parent molecular species has a value for said molecular weight (Mr) not less than 7000.

89. A composition of matter comprising one or more distinct populations of multiply charged polyatomic ions, each of said multiply charged polyatomic ions in said distinct populations being characterized by the symbol xi, the numerical value of xi being the m/z value of said one of said multiply charged ions such that xi=Mr/i+ma wherein Mr is the molecular weight of a distinct parent polyatomic molecular species from which all of said multiply charged polyatomic ions in said distinct population of multiply charged polyatomic ions are derived, i is an integer equal to the number of adduct charges attached to a molecule of said distinct parent polyatomic_molecular species_to form one of said multiply charged polyatomic ions, and ma is the effective average mass (which can sometimes be negative) of each said adduct charge, each of said distinct populations of multiply charged polyatomic ions comprising a plurality of sub-populations, the ions of each sub-population having the same values for i, ma and Mr and therefore the same value of xi, said distinct populations of multiply charged polyatomic ions including at least one population in which all the ions have values of i greater than three.

90. The composition of matter of claim 89 in which all the ions in said at least one population have values of i greater than six.

91. The composition of matter of claim 89 in which at least one of said distinct polyatomic parent molecular species is selected from a class of compounds known as biopolymers.

92. The composition of matter of claim 89 such that the mass spectrum of the ions in at least one of said distinct populations of multiply charged polyatomic ions, formed from at least one of said distinct polyatomic parent molecular species, comprises a sequence of peaks, one peak for each value of xi found by mass analysis of the ions of said distinct population of multiply charged polyatomic ions, the set of values for xi including one for each value of i beginning with a smallest value of not less than four and extending to a largest value not less than seven.

93. The composition of matter of claim 89 in which at least one of said distinct polyatomic parent molecular species has a value of said molecular weight, Mr, not less than 5000.

94. The composition of matter of claim 89 in which at least one of said distinct polyatomic parent molecular species has a value of said molecular weight, Mr, not less than 7000.

95. A composition of matter comprising one or more distinct populations of multiply charged polyatomic ions, each one of said multiply charged polyatomic ions in said one or more distinct populations being characterized by the symbol xi, the numerical value of xi being the m/z value of said multiply charged polyatomic ion such that xi=Mr/i+ma wherein Mr is the molecular weight of a distinct parent polyatomic molecular species from which all of said multiply charged polyatomic ions in one of said distinct populations of multiply charged polyatomic ions are derived, i is an integer equal to the number of individual adduct charges attached to a molecule of said distinct parent polyatomic molecular species to form one of said multiply charged polyatomic ions, ma is the effective average mass of said individual adduct charges (which can be negative), each of said distinct populations of ions comprising a plurality of sub-populations, the ions of each sub-population having the same values for i, ma and Mr and therefore the same value of xi, the value of i being at least three for every ion in at least one of said distinct populations of multiply charged polyatomic ions, said composition of matter being formed by:

dispersing a solution containing said polyatomic parent molecular species into a bath gas as charged droplets, said dispersing taking place in the presence of an electric field, and allowing the solvent of said solution to evaporate from said charged droplets until at least some molecules of said parent polyatomic parent molecular species become dispersed in said bath gas as said multiply charged ions.

96. The composition of matter of claim 95 in which every ion in at least one of said distinct populations of multiply charged polyatomic ions has a value of i not less than five.

97. The composition of matter of claim 95 in which every ion in at least one of said distinct populations of multiply charged polyatomic ions has a value of i not less than seven.

98. The composition of matter of claim 95 in which at least one of said distinct polyatomic parent molecular species is selected from a class of compounds known as biopolymers.

99. The composition of matter of claim 95 in which at least one of said distinct polyatomic parent molecular species is not selected from the-group comprising poly (ethylene glycol)s.

100. The composition of matter of claim 95 in which at least one of said distinct polyatomic parent molecular species has a value of said molecular weight, Mr, not less than 5000.

101. A composition of matter comprising one or more populations of polyatomic gaseous ions, at least one of said populations comprising multiply charged ions formed from the same chemically distinct parent species of polyatomic neutral molecules, said same chemically distinct species of polyatomic neutral molecules not including synthetic polymers such as poly (ethylene glycol)s, all of said multiply charged ions, formed from said same chemically distinct species of polyatomic neutral molecules, having at least three charges.

102. A composition of matter according to claim 101 in which all of said multiply charged polyatomic ions, formed from said chemically distinct species of polyatomic neutral molecules, have at least five charges.

103. A composition of matter according to claim 101 in which all of said multiply charged polyatomic ions, formed from, said chemically distinct species of polyatomic neutral molecules, have at least seven charges.

104. A composition of matter comprising one or more populations of polyatomic gaseous ions, at least one of said populations of polyatomic ions comprising multiply charged ions formed from the same chemically distinct parent species of polyatomic neutral molecules, said chemically distinct parent species of polyatomic molecules not being selected from the class comprising oligomers of synthetic polymers such as poly (ethylene glycol)s, the number of charges on each ion defining the charge state number of that ion, said at least one of said populations of polyatomic multiply charged ions comprising a plurality of sub-populations, one such sub-population for each possible integral value of charge state number beginning with a smallest value not less than three and extending to a largest value not less than five.

105. A composition of matter according to claim 104 in which said smallest value of charge state number is not less than five and said largest value is not less than seven.

106. A composition of matter according to claim 104 in which said smallest value of charge state number is not less than seven and said largest value is not less than ten.

107. A composition of matter comprising one or more populations of polyatomic gaseous ions, all of the ions in at least one of said populations comprising multiply charged polyatomic ions having a net charge equal to or greater than three elementary charges and a composition characterized by the empirical chemical formula (Cc Hh Nn Oo Ss Pp Tt Uu Vv Ww Yy) wherein upper case letters C, H, N, O, S, P stand respectively for the elements Carbon, Hydrogen, Nitrogen, Oxygen, Sulfur, Phosphorous and T, U, V, W, Y each stand for other elements in the Periodic Table, the lower case subscript letters associated with each of said upper case letters symbolizing an integer equal to the number of atoms of the corresponding element in said ion, all the ions with three or more charges in at least one of said one or more populations of ions having compositions such that the number of different subscripts c, h, o, n, p, s, t, u, v, w, y having values greater than zero is five or less, said ions not being derived from a member of the class of synthetic polymers that include poly (ethylene glycol)s.

108. A composition of matter as in claim 107 in which all the ions in said at least one population of multiply charged polyatomic ions have at least five charges.

109. A composition of matter as in claim 107 in which all the ions in said at least one population of multiply charged polyatomic ions have at least seven charges.

110. A composition of matter comprising one or more populations of gaseous ions, at least one of said populations comprising multiply charged polyatomic ions having a net charge equal to or greater than three elementary charges and a composition characterized by the empirical chemical formula (Cc Hh Nn Oo Ss Pp Tt Uu Vv Ww Yy) wherein upper case letters C, H, N, O, S, P stand respectively for the elements Carbon, Hydrogen, Nitrogen, Oxygen, Sulfur, Phosphorous and T, U, V, W, Y each stand for other elements in the Periodic Table, the lower case letters symbolizing an integer equal to the number of atoms of the corresponding element in said ion, all the ions with three or more charges in at least one of said one or more populations of polyatomic ions having compositions such that the number of different subscripts c, h, n, o, p, s, t, u, v, w, y having values greater than zero is greater than five.

111. A composition of matter as in claim 110 in which all the ions in said at least one population of multiply charged polyatomic ions have at least five charges and a composition such that the number of different subscripts c, h, n, o, p, s, t, u, v, w, y having values greater than zero is greater than five.

112. A composition of matter as in claim 110 in which all the ions in said at least one population of multiply charged polyatomic ions have at least seven charges and a composition such that the number of different subscripts c, h, n, o, p, s, t, u, v, w having values greater than zero is greater than five.

* * * * *

UNITED STATES PATENT AND TRADEMARK OFFICE
CERTIFICATE OF CORRECTION

PATENT NO.       : 5,686,726
APPLICATION NO.  : 07/911405
DATED            : November 11, 1997
INVENTOR(S)      : John B. Fenn et al.

Page 1 of 1

It is certified that error appears in the above-identified patent and that said Letters Patent is hereby corrected as shown below:

Please correct the Government Rights Statement in Col. 1 lines 12-14 as shown below:

"This invention was made with government support under 2RO1GM031660-04A1 awarded by the National Institutes of Health. The government has certain rights in the invention."

Signed and Sealed this

Fifth Day of May, 2009

JOHN DOLL
*Acting Director of the United States Patent and Trademark Office*

(12) EX PARTE REEXAMINATION CERTIFICATE (10469th)
United States Patent
Fenn et al.

(10) Number: US 5,686,726 C1
(45) Certificate Issued: Jan. 12, 2015

(54) COMPOSITION OF MATTER OF A POPULATION OF MULTIPLY CHARGED IONS DERIVED FROM POLYATOMIC PARENT MOLECULAR SPECIES

(75) Inventors: John Bennett Fenn, Branford, CT (US); Chin-Kai Meng, Hockessin, DE (US); Matthias Mann, Odense (DK)

(73) Assignee: The United States of America, as represented by the National Institutes of Health (NIH), Dept. of Health and Human Services (DHHS), Washington, DC (US)

Reexamination Request:
No. 90/020,008, Jul. 17, 2012

Reexamination Certificate for:
Patent No.: 5,686,726
Issued: Nov. 11, 1997
Appl. No.: 07/911,405
Filed: Jul. 10, 1992

Certificate of Correction issued May 5, 2009

Related U.S. Application Data

(60) Division of application No. 07/773,776, filed on Oct. 10, 1991, now Pat. No. 5,130,538, which is a continuation of application No. 07/683,105, filed on Apr. 10, 1991, now abandoned, which is a continuation of application No. 07/354,393, filed on May 19, 1989, now abandoned.

(51) Int. Cl.
*H01J 49/04* (2006.01)
*H01J 49/02* (2006.01)

(52) U.S. Cl.
USPC ........................................ 250/282; 250/281

(58) Field of Classification Search
None
See application file for complete search history.

(56) References Cited

To view the complete listing of prior art documents cited during the proceeding for Reexamination Control Number 90/020,008, please refer to the USPTO's public Patent Application Information Retrieval (PAIR) system under the Display References tab.

*Primary Examiner* — Hetul Patel

(57) ABSTRACT

This invention describes the production of mass spectra which contain a multiplicity of peaks. The component ions of these peaks, which are multiply charged, are formed by dispersing a solution containing an analyte into a bath gas as highly charged droplets. The analyte is generally a compound of high molecular weight and is of biochemical interest. The invention also describes methods for calculating the molecular weight of the analyte from the measured mass values of the highly charged ions.

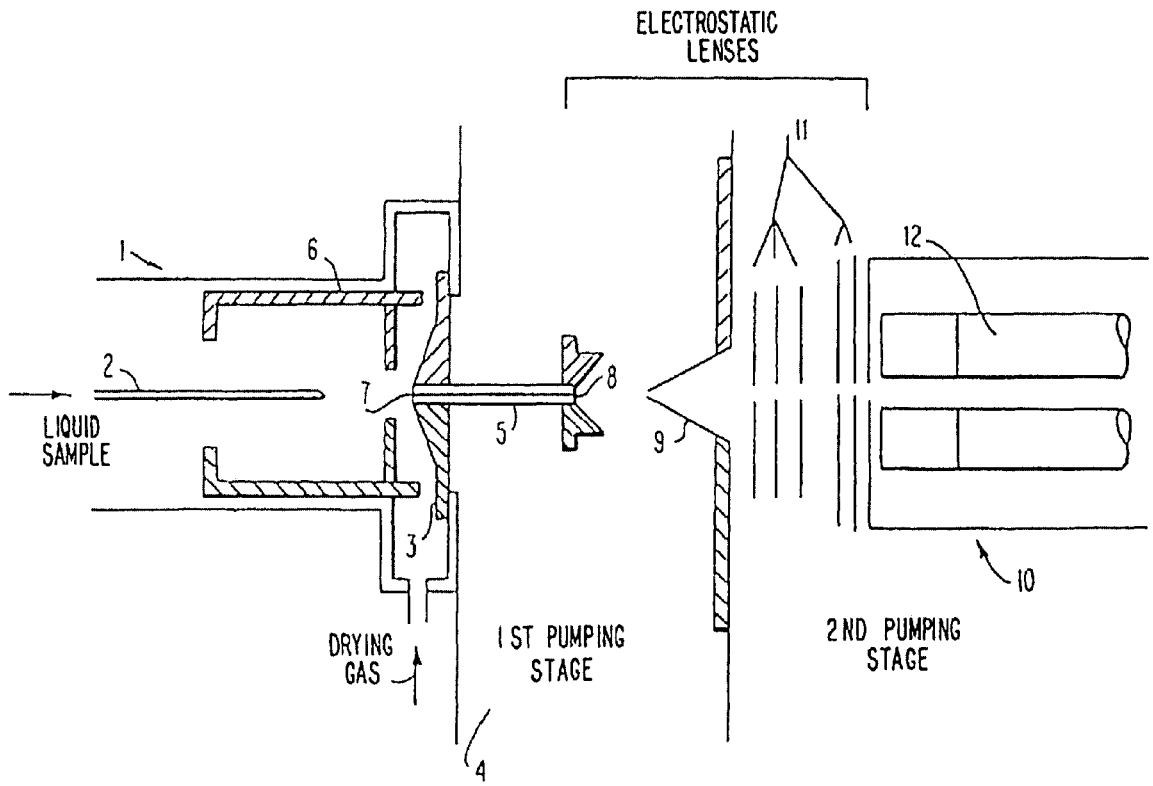

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-112 are cancelled.

\* \* \* \* \*